United States Patent
DeBenedictis et al.

(10) Patent No.: US 10,575,890 B2
(45) Date of Patent: Mar. 3, 2020

(54) TREATMENT SYSTEMS AND METHODS FOR AFFECTING GLANDS AND OTHER TARGETED STRUCTURES

(71) Applicant: ZELTIQ AESTHESTIC, INC., Pleasanton, CA (US)

(72) Inventors: Leonard DeBenedictis, Dublin, CA (US); George Frangineas, Jr., Fremont, CA (US); Kristine Tatsutani, Redwood City, CA (US); Bryan J. Weber, Livermore, CA (US); Kerrie Jiang, Foster City, CA (US); Peter Yee, San Ramon, CA (US); Linda Pham, Pleasanton, CA (US); Gurvinder Singh Nanda, Fremont, CA (US)

(73) Assignee: Zeltiq Aesthetics, Inc., Pleasanton, CA (US)

( * ) Notice: Subject to any disclaimer, the term of this patent is extended or adjusted under 35 U.S.C. 154(b) by 626 days.

(21) Appl. No.: 15/115,503

(22) PCT Filed: Jan. 30, 2015

(86) PCT No.: PCT/US2015/013971
§ 371 (c)(1),
(2) Date: Jul. 29, 2016

(87) PCT Pub. No.: WO2015/117032
PCT Pub. Date: Aug. 6, 2015

(65) Prior Publication Data
US 2017/0007309 A1    Jan. 12, 2017

Related U.S. Application Data

(60) Provisional application No. 61/934,549, filed on Jan. 31, 2014, provisional application No. 61/943,257, (Continued)

(51) Int. Cl.
*A61B 18/02* (2006.01)
*A61F 7/00* (2006.01)
(Continued)

(52) U.S. Cl.
CPC .......... *A61B 18/02* (2013.01); *A61B 18/0206* (2013.01); *A61B 90/04* (2016.02);
(Continued)

(58) Field of Classification Search
CPC ............ A61B 18/02; A61B 2018/0237; A61B 2018/00005; A61B 2018/00023;
(Continued)

(56) References Cited

U.S. PATENT DOCUMENTS

| | | |
|---|---|---|
| 681,806 A | 9/1901 | Mignault et al. |
| 889,810 A | 6/1908 | Robinson et al. |

(Continued)

FOREIGN PATENT DOCUMENTS

| | | |
|---|---|---|
| AU | 2011253768 A1 | 6/2012 |
| CA | 2441489 A1 | 3/2005 |

(Continued)

OTHER PUBLICATIONS

"ThermaCool Monopolar Capacitive Radiofrequency, The one choice for nonablative tissue tightening and contouring", Thermage, Inc. Tech Brochure, Nov. 30, 2005, 8 pgs.
(Continued)

*Primary Examiner* — Thomas A Giuliani
(74) *Attorney, Agent, or Firm* — Perkins Coie LLP

(57) ABSTRACT

Treatment systems, methods, and apparatuses for treating acne, hyperhidrosis, and other skin conditions are described. Aspects of the technology can include cooling a surface of a patient's skin and detecting changes in the tissue. The tissue can be cooled a sufficient length of time and to a (Continued)

temperature low enough to affect glands or other targeted structures in the skin.

13 Claims, 8 Drawing Sheets

Related U.S. Application Data filed on Feb. 21, 2014, provisional application No. 61/943,250, filed on Feb. 21, 2014.

(51) Int. Cl.

| | |
|---|---|
| *A61H 1/00* | (2006.01) |
| *A61N 7/00* | (2006.01) |
| *A61K 31/045* | (2006.01) |
| *A61K 31/047* | (2006.01) |
| *A61B 90/00* | (2016.01) |
| *A61B 18/00* | (2006.01) |

(52) U.S. Cl.
CPC .............. *A61F 7/00* (2013.01); *A61F 7/007* (2013.01); *A61H 1/006* (2013.01); *A61H 1/008* (2013.01); *A61K 31/045* (2013.01); *A61K 31/047* (2013.01); *A61N 7/00* (2013.01); *A61B 2018/00291* (2013.01); *A61B 2018/00464* (2013.01); *A61B 2018/00714* (2013.01); *A61B 2018/00791* (2013.01); *A61B 2018/00875* (2013.01); *A61B 2018/00994* (2013.01); *A61B 2018/0237* (2013.01); *A61B 2018/0262* (2013.01); *A61B 2090/0463* (2016.02); *A61B 2090/065* (2016.02); *A61F 2007/0003* (2013.01); *A61F 2007/0004* (2013.01); *A61F 2007/0019* (2013.01); *A61F 2007/0036* (2013.01); *A61F 2007/0045* (2013.01); *A61F 2007/0047* (2013.01); *A61F 2007/0052* (2013.01); *A61F 2007/0056* (2013.01); *A61F 2007/0075* (2013.01); *A61F 2007/0087* (2013.01); *A61F 2007/0093* (2013.01); *A61F 2007/0096* (2013.01)

(58) Field of Classification Search
CPC ........... A61B 2018/00041; A61B 2018/00452; A61B 2018/00458; A61B 2018/0047; A61B 2018/00476; A61B 2018/0262; A61B 90/04; A61B 2090/0463; A61F 7/00; A61F 2007/0052; A61F 2007/0093; A61F 2007/0056
USPC ........................................ 607/96; 606/20–26
See application file for complete search history.

(56) References Cited

U.S. PATENT DOCUMENTS

| | | |
|---|---|---|
| 1,093,868 A | 4/1914 | Leighty |
| 2,516,491 A | 7/1950 | Swastek |
| 2,521,780 A | 9/1950 | Dodd et al. |
| 2,726,658 A | 12/1955 | Chessey |
| 2,766,619 A | 10/1956 | Tribus et al. |
| 2,851,602 A | 9/1958 | Cramwinckel et al. |
| 3,093,135 A | 6/1963 | Hirschhorn |
| 3,132,688 A | 5/1964 | Nowak |
| 3,133,539 A | 5/1964 | William et al. |
| 3,282,267 A | 11/1966 | Eidus |
| 3,341,230 A | 9/1967 | Wichers |
| 3,502,080 A | 3/1970 | Hirschhorn |
| 3,587,577 A | 6/1971 | Zubkov et al. |
| 3,591,645 A | 7/1971 | Selwitz |
| 3,692,338 A | 9/1972 | Didier |
| 3,703,897 A | 11/1972 | Mack et al. |
| 3,710,784 A | 1/1973 | Taylor |
| 3,786,814 A | 1/1974 | Armao |
| 3,827,436 A | 8/1974 | Andera et al. |
| 3,942,519 A | 3/1976 | Shock |
| 3,948,269 A | 4/1976 | Zimmer |
| 3,986,385 A | 10/1976 | Johnston et al. |
| 3,993,053 A | 11/1976 | Grossan |
| 4,002,221 A | 1/1977 | Buchalter |
| 4,008,910 A | 2/1977 | Roche |
| 4,026,299 A | 5/1977 | Sauder |
| 4,140,130 A | 2/1979 | Storm |
| 4,149,529 A | 4/1979 | Copeland et al. |
| 4,178,429 A | 12/1979 | Scheffer |
| 4,202,336 A | 5/1980 | Van Gerven |
| 4,266,043 A | 5/1981 | Fujii et al. |
| 4,269,068 A | 5/1981 | Molina |
| 4,381,009 A | 4/1983 | Del Bon |
| 4,396,011 A | 8/1983 | Mack et al. |
| 4,459,854 A | 7/1984 | Richardson et al. |
| 4,470,263 A | 9/1984 | Lehovec et al. |
| 4,483,341 A | 11/1984 | Witteles |
| 4,528,979 A | 7/1985 | Marchenko et al. |
| 4,531,524 A | 7/1985 | Mioduski |
| 4,548,212 A | 10/1985 | Leung |
| 4,555,313 A | 11/1985 | Duchane et al. |
| 4,585,002 A | 4/1986 | Kissin |
| 4,603,076 A | 7/1986 | Bowditch et al. |
| 4,614,191 A | 9/1986 | Perler et al. |
| 4,644,955 A | 2/1987 | Mioduski |
| 4,664,110 A | 5/1987 | Schanzlin |
| 4,700,701 A | 10/1987 | Montaldi |
| 4,718,429 A | 1/1988 | Smidt |
| 4,741,338 A | 5/1988 | Miyamae |
| 4,758,217 A | 7/1988 | Gueret |
| 4,764,463 A | 8/1988 | Mason et al. |
| 4,802,475 A | 2/1989 | Weshahy |
| 4,832,022 A | 5/1989 | Tjulkov et al. |
| 4,846,176 A | 7/1989 | Golden |
| 4,850,340 A | 7/1989 | Onishi |
| 4,869,250 A | 9/1989 | Bitterly |
| 4,880,564 A | 11/1989 | Abel et al. |
| 4,905,697 A | 3/1990 | Heggs et al. |
| 4,906,463 A | 3/1990 | Cleary et al. |
| 4,930,317 A | 6/1990 | Klein |
| 4,935,345 A | 6/1990 | Guilbeau et al. |
| 4,961,422 A | 10/1990 | Marchosky et al. |
| 4,962,761 A | 10/1990 | Golden |
| 4,990,144 A | 2/1991 | Blott et al. |
| 5,007,433 A | 4/1991 | Hermsdoerffer et al. |
| 5,018,521 A | 5/1991 | Campbell et al. |
| 5,024,650 A | 6/1991 | Hagiwara et al. |
| 5,065,752 A | 11/1991 | Sessions et al. |
| 5,069,208 A | 12/1991 | Noppel et al. |
| 5,084,671 A | 1/1992 | Miyata et al. |
| 5,108,390 A | 4/1992 | Potocky et al. |
| 5,119,674 A | 6/1992 | Nielsen |
| 5,139,496 A | 8/1992 | Hed |
| 5,143,063 A | 9/1992 | Fellner |
| 5,148,804 A | 9/1992 | Hill et al. |
| 5,158,070 A | 10/1992 | Dory |
| 5,169,384 A | 12/1992 | Bosniak et al. |
| 5,197,466 A | 3/1993 | Marchosky et al. |
| 5,207,674 A | 5/1993 | Hamilton |
| 5,221,726 A | 6/1993 | Dabi et al. |
| 5,264,234 A | 11/1993 | Windhab et al. |
| 5,277,030 A | 1/1994 | Miller |
| 5,314,423 A | 5/1994 | Seney et al. |
| 5,327,886 A | 7/1994 | Chiu |
| 5,330,745 A | 7/1994 | Mcdow et al. |
| 5,333,460 A | 8/1994 | Lewis et al. |
| 5,334,131 A | 8/1994 | Omandam et al. |
| 5,336,616 A | 8/1994 | Livesey et al. |
| 5,339,541 A | 8/1994 | Owens |
| 5,342,617 A | 8/1994 | Gold et al. |
| 5,351,677 A | 10/1994 | Kami et al. |
| 5,358,467 A | 10/1994 | Milstein et al. |
| 5,362,966 A | 11/1994 | Rosenthal et al. |
| 5,363,347 A | 11/1994 | Nguyen |
| 5,372,608 A | 12/1994 | Johnson |

(56) References Cited

U.S. PATENT DOCUMENTS

| | | |
|---|---|---|
| 5,386,837 A | 2/1995 | Sterzer |
| 5,411,541 A | 5/1995 | Bell et al. |
| 5,427,772 A | 6/1995 | Hagan et al. |
| 5,433,717 A | 7/1995 | Rubinsky et al. |
| 5,456,703 A | 10/1995 | Beeuwkes, III et al. |
| 5,472,416 A | 12/1995 | Blugerman et al. |
| 5,486,207 A | 1/1996 | Mahawili |
| 5,497,596 A | 3/1996 | Zatkulak |
| 5,501,655 A | 3/1996 | Rolt et al. |
| 5,505,726 A | 4/1996 | Meserol |
| 5,505,730 A | 4/1996 | Edwards et al. |
| 5,507,790 A | 4/1996 | Weiss |
| 5,514,105 A | 5/1996 | Goodman, Jr. et al. |
| 5,514,170 A | 5/1996 | Mauch |
| 5,516,505 A | 5/1996 | McDow |
| 5,531,742 A | 7/1996 | Barken |
| 5,558,376 A | 9/1996 | Woehl |
| 5,562,604 A | 10/1996 | Yablon et al. |
| 5,571,801 A | 11/1996 | Segall et al. |
| 5,575,812 A | 11/1996 | Owens et al. |
| 5,603,221 A | 2/1997 | Maytal |
| 5,628,769 A | 5/1997 | Saringer |
| 5,634,890 A | 6/1997 | Morris |
| 5,634,940 A | 6/1997 | Panyard |
| 5,647,051 A | 7/1997 | Neer |
| 5,647,868 A | 7/1997 | Chinn |
| 5,650,450 A | 7/1997 | Lovette et al. |
| 5,651,773 A | 7/1997 | Perry et al. |
| 5,654,279 A | 8/1997 | Rubinsky et al. |
| 5,654,546 A | 8/1997 | Lindsay et al. |
| 5,660,836 A | 8/1997 | Knowlton et al. |
| 5,665,053 A | 9/1997 | Jacobs |
| 5,672,172 A | 9/1997 | Zupkas |
| 5,700,284 A | 12/1997 | Owens et al. |
| 5,725,483 A | 3/1998 | Podolsky |
| 5,733,280 A | 3/1998 | Avitall |
| 5,741,248 A | 4/1998 | Stern et al. |
| 5,746,702 A | 5/1998 | Gelfgat et al. |
| 5,746,736 A | 5/1998 | Tankovich |
| 5,755,663 A | 5/1998 | Larsen et al. |
| 5,755,753 A | 5/1998 | Knowlton et al. |
| 5,755,755 A | 5/1998 | Panyard |
| 5,759,182 A | 6/1998 | Varney et al. |
| 5,759,764 A | 6/1998 | Polovina et al. |
| 5,769,879 A | 6/1998 | Richards et al. |
| 5,785,955 A | 7/1998 | Fischer |
| 5,792,080 A | 8/1998 | Ookawa et al. |
| 5,800,490 A | 9/1998 | Patz et al. |
| 5,814,040 A | 9/1998 | Nelson et al. |
| 5,817,050 A | 10/1998 | Klein et al. |
| 5,817,149 A | 10/1998 | Owens et al. |
| 5,817,150 A | 10/1998 | Owens et al. |
| 5,830,208 A | 11/1998 | Muller et al. |
| 5,833,685 A | 11/1998 | Tortal et al. |
| 5,844,013 A | 12/1998 | Kenndoff et al. |
| 5,853,364 A | 12/1998 | Baker et al. |
| 5,865,841 A | 2/1999 | Kolen et al. |
| 5,871,524 A | 2/1999 | Knowlton |
| 5,871,526 A | 2/1999 | Gibbs et al. |
| 5,885,211 A | 3/1999 | Eppstein et al. |
| 5,891,617 A | 4/1999 | Watson et al. |
| 5,895,418 A | 4/1999 | Saringer |
| 5,901,707 A | 5/1999 | Goncalves |
| 5,902,256 A | 5/1999 | Benaron |
| 5,919,219 A | 7/1999 | Knowlton et al. |
| 5,944,748 A | 8/1999 | Mager et al. |
| 5,948,011 A | 9/1999 | Knowlton et al. |
| 5,954,680 A | 9/1999 | Augustine et al. |
| 5,964,092 A | 10/1999 | Tozuka et al. |
| 5,964,749 A | 10/1999 | Eckhouse et al. |
| 5,967,976 A | 10/1999 | Larsen et al. |
| 5,980,561 A | 11/1999 | Kolen et al. |
| 5,986,167 A | 11/1999 | Arteman et al. |
| 5,989,286 A | 11/1999 | Owens et al. |
| 5,997,530 A | 12/1999 | Nelson et al. |
| 6,017,337 A | 1/2000 | Pira |
| 6,023,932 A | 2/2000 | Johnston |
| 6,032,675 A | 3/2000 | Rubinsky |
| 6,039,694 A | 3/2000 | Larson et al. |
| 6,041,787 A | 3/2000 | Rubinsky |
| 6,047,215 A | 4/2000 | McClure et al. |
| 6,049,927 A | 4/2000 | Thomas et al. |
| 6,051,159 A | 4/2000 | Hao et al. |
| 6,071,239 A | 6/2000 | Cribbs et al. |
| 6,074,415 A | 6/2000 | Der Ovanesian |
| 6,093,230 A | 7/2000 | Johnson et al. |
| 6,102,885 A | 8/2000 | Bass |
| 6,104,952 A | 8/2000 | Tu et al. |
| 6,104,959 A | 8/2000 | Spertell et al. |
| 6,106,517 A | 8/2000 | Zupkas |
| 6,113,558 A | 9/2000 | Rosenschein et al. |
| 6,113,559 A | 9/2000 | Klopotek |
| 6,113,626 A | 9/2000 | Clifton et al. |
| 6,120,519 A | 9/2000 | Weber et al. |
| 6,139,544 A | 10/2000 | Mikus et al. |
| 6,150,148 A | 11/2000 | Nanda et al. |
| 6,151,735 A | 11/2000 | Koby et al. |
| 6,152,952 A | 11/2000 | Owens et al. |
| 6,171,301 B1 | 1/2001 | Nelson et al. |
| 6,180,867 B1 | 1/2001 | Hedengren et al. |
| 6,226,996 B1 | 5/2001 | Weber et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van Vilsteren et al. |
| 6,311,090 B1 | 10/2001 | Knowlton |
| 6,311,497 B1 | 11/2001 | Chung |
| 6,312,453 B1 | 11/2001 | Stefanile et al. |
| 6,350,276 B1 | 2/2002 | Knowlton |
| 6,354,297 B1 | 3/2002 | Eiseman |
| 6,357,907 B1 | 3/2002 | Cleveland et al. |
| 6,375,673 B1 | 4/2002 | Clifton et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,401,722 B1 | 6/2002 | Krag |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,430,956 B1 | 8/2002 | Haas et al. |
| 6,438,424 B1 | 8/2002 | Knowlton |
| 6,438,954 B1 | 8/2002 | Goetz et al. |
| 6,438,964 B1 | 8/2002 | Giblin |
| 6,453,202 B1 | 9/2002 | Knowlton |
| 6,458,888 B1 | 10/2002 | Hood et al. |
| 6,461,378 B1 | 10/2002 | Knowlton |
| 6,470,216 B1 | 10/2002 | Knowlton |
| 6,471,693 B1 | 10/2002 | Carroll et al. |
| 6,475,211 B2 | 11/2002 | Chess et al. |
| 6,478,811 B1 | 11/2002 | Dobak, III et al. |
| 6,494,844 B1 | 12/2002 | Van Bladel et al. |
| 6,497,721 B2 | 12/2002 | Ginsburg et al. |
| 6,508,831 B1 | 1/2003 | Kushnir |
| 6,514,244 B2 | 2/2003 | Pope et al. |
| 6,519,964 B2 | 2/2003 | Bieberich |
| 6,523,354 B1 | 2/2003 | Tolbert |
| 6,527,765 B2 | 3/2003 | Kelman et al. |
| 6,527,798 B2 | 3/2003 | Ginsburg et al. |
| 6,544,248 B1 | 4/2003 | Bass |
| 6,547,811 B1 | 4/2003 | Becker et al. |
| 6,548,297 B1 | 4/2003 | Kuri-Harcuch et al. |
| 6,551,255 B2 | 4/2003 | Van Bladel et al. |
| 6,551,341 B2 | 4/2003 | Boylan et al. |
| 6,551,348 B1 | 4/2003 | Blalock et al. |
| 6,551,349 B2 | 4/2003 | Lasheras et al. |
| 6,569,189 B1 | 5/2003 | Augustine et al. |
| 6,585,652 B2 | 7/2003 | Lang et al. |
| 6,592,577 B2 | 7/2003 | Abboud et al. |
| 6,605,080 B1 | 8/2003 | Altshuler et al. |
| 6,607,498 B2 | 8/2003 | Eshel |

(56) References Cited

U.S. PATENT DOCUMENTS

| | | |
|---|---|---|
| 6,620,187 B2 | 9/2003 | Carson et al. |
| 6,620,188 B1 | 9/2003 | Ginsburg et al. |
| 6,620,189 B1 | 9/2003 | Machold et al. |
| 6,623,430 B1 | 9/2003 | Slayton et al. |
| 6,626,854 B2 | 9/2003 | Friedman et al. |
| 6,632,219 B1 | 10/2003 | Baranov et al. |
| 6,635,053 B1 | 10/2003 | Lalonde et al. |
| 6,643,535 B2 | 11/2003 | Damasco et al. |
| 6,645,162 B2 | 11/2003 | Friedman et al. |
| 6,645,229 B2 | 11/2003 | Matsumura et al. |
| 6,645,232 B2 | 11/2003 | Carson |
| 6,648,904 B2 | 11/2003 | Altshuler et al. |
| 6,656,208 B2 | 12/2003 | Grahn et al. |
| 6,660,027 B2 | 12/2003 | Gruszecki et al. |
| 6,662,054 B2 | 12/2003 | Kreindel et al. |
| 6,682,550 B2 | 1/2004 | Clifton et al. |
| 6,685,731 B2 | 2/2004 | Kushnir et al. |
| 6,694,170 B1 | 2/2004 | Mikus et al. |
| 6,695,874 B2 | 2/2004 | Machold et al. |
| 6,697,670 B2 | 2/2004 | Chornenky |
| 6,699,237 B2 | 3/2004 | Weber et al. |
| 6,699,266 B2 | 3/2004 | Lachenbruch et al. |
| 6,699,267 B2 | 3/2004 | Voorhees et al. |
| 6,718,785 B2 | 4/2004 | Bieberich |
| 6,741,895 B1 | 5/2004 | Gafni et al. |
| 6,743,222 B2 | 6/2004 | Durkin et al. |
| 6,746,474 B2 | 6/2004 | Saadat |
| 6,749,624 B2 | 6/2004 | Knowlton |
| 6,764,493 B1 | 7/2004 | Weber et al. |
| 6,764,502 B2 | 7/2004 | Bieberich |
| 6,789,545 B2 | 9/2004 | Littrup et al. |
| 6,795,728 B2 | 9/2004 | Chornenky et al. |
| 6,820,961 B2 | 11/2004 | Johnson |
| 6,821,274 B2 | 11/2004 | McHale et al. |
| 6,840,955 B2 | 1/2005 | Ein |
| 6,849,075 B2 | 2/2005 | Bertolero et al. |
| 6,878,144 B2 | 4/2005 | Altshuler et al. |
| 6,889,090 B2 | 5/2005 | Kreindel |
| 6,892,099 B2 | 5/2005 | Jaafar et al. |
| 6,904,956 B2 | 6/2005 | Noel |
| 6,918,903 B2 | 7/2005 | Bass |
| 6,927,316 B1 | 8/2005 | Faries, Jr. et al. |
| 6,942,022 B2 | 9/2005 | Blangetti et al. |
| 6,945,942 B2 | 9/2005 | Van Bladel et al. |
| 6,948,903 B2 | 9/2005 | Ablabutyan et al. |
| 6,969,399 B2 | 11/2005 | Schock et al. |
| 7,005,558 B1 | 2/2006 | Johansson et al. |
| 7,006,874 B2 | 2/2006 | Knowlton et al. |
| 7,022,121 B2 | 4/2006 | Stern et al. |
| 7,037,326 B2 | 5/2006 | Lee |
| 7,054,685 B2 | 5/2006 | Dimmer et al. |
| 7,060,061 B2 | 6/2006 | Altshuler et al. |
| 7,077,858 B2 | 7/2006 | Fletcher et al. |
| 7,081,111 B2 | 7/2006 | Svaasand et al. |
| 7,083,612 B2 | 8/2006 | Littrup et al. |
| 7,096,204 B1 | 8/2006 | Chen et al. |
| 7,112,712 B1 | 9/2006 | Ancell |
| 7,115,123 B2 | 10/2006 | Knowlton et al. |
| 7,141,049 B2 | 11/2006 | Stern et al. |
| 7,183,360 B2 | 2/2007 | Daniel et al. |
| 7,189,252 B2 | 3/2007 | Krueger |
| 7,192,426 B2 | 3/2007 | Baust et al. |
| 7,204,832 B2 | 4/2007 | Altshuler et al. |
| 7,220,778 B2 | 5/2007 | Anderson et al. |
| 7,229,436 B2 | 6/2007 | Stern et al. |
| 7,258,674 B2 | 8/2007 | Cribbs et al. |
| 7,267,675 B2 | 9/2007 | Stern et al. |
| 7,276,058 B2 | 10/2007 | Altshuler et al. |
| 7,318,821 B2 | 1/2008 | Lalonde et al. |
| 7,331,951 B2 | 2/2008 | Eshel et al. |
| 7,347,855 B2 | 3/2008 | Eshel et al. |
| 7,367,341 B2 | 5/2008 | Anderson et al. |
| 7,532,201 B2 | 5/2009 | Quistgaard et al. |
| 7,572,268 B2 | 8/2009 | Babaev |
| 7,604,632 B2 | 10/2009 | Howlett et al. |
| 7,613,523 B2 | 11/2009 | Eggers et al. |
| 7,615,016 B2 | 11/2009 | Barthe et al. |
| 7,713,266 B2 | 5/2010 | Elkins et al. |
| 7,780,656 B2 | 8/2010 | Tankovich |
| 7,799,018 B2 | 9/2010 | Goulko |
| 7,824,437 B1 | 11/2010 | Saunders |
| 7,828,831 B1 | 11/2010 | Tanhehco et al. |
| 7,850,683 B2 | 12/2010 | Elkins et al. |
| 7,854,754 B2 | 12/2010 | Ting et al. |
| 7,862,558 B2 | 1/2011 | Elkins et al. |
| RE42,277 E | 4/2011 | Jaafar et al. |
| 7,938,824 B2 | 5/2011 | Chornenky et al. |
| 7,959,657 B1 | 6/2011 | Harsy et al. |
| 7,963,959 B2 | 6/2011 | Da Silva et al. |
| 7,967,763 B2 | 6/2011 | Deem et al. |
| 7,993,330 B2 | 8/2011 | Goulko |
| 7,998,137 B2 | 8/2011 | Elkins et al. |
| RE42,835 E | 10/2011 | Chornenky et al. |
| RE43,009 E | 12/2011 | Chornenky et al. |
| 8,133,180 B2 | 3/2012 | Slayton et al. |
| 8,133,191 B2 | 3/2012 | Rosenberg et al. |
| 8,192,474 B2 | 6/2012 | Levinson |
| 8,246,611 B2 | 8/2012 | Paithankar et al. |
| 8,275,442 B2 | 9/2012 | Allison |
| 8,285,390 B2 | 10/2012 | Levinson et al. |
| 8,333,700 B1 | 12/2012 | Barthe et al. |
| 8,337,539 B2 | 12/2012 | Ting et al. |
| 8,366,622 B2 | 2/2013 | Slayton et al. |
| 8,372,130 B2 | 2/2013 | Young et al. |
| 8,397,518 B1 | 3/2013 | Vistakula et al. |
| 8,414,631 B2 | 4/2013 | Quisenberry et al. |
| 8,433,400 B2 | 4/2013 | Prushinskaya et al. |
| 8,506,486 B2 | 8/2013 | Slayton et al. |
| 8,523,775 B2 | 9/2013 | Barthe et al. |
| 8,523,791 B2 | 9/2013 | Castel |
| 8,523,927 B2 | 9/2013 | Levinson et al. |
| 8,535,228 B2 | 9/2013 | Slayton et al. |
| 8,603,073 B2 | 12/2013 | Allison |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,676,332 B2 | 3/2014 | Fahey |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,702,774 B2 | 4/2014 | Baker et al. |
| 8,758,215 B2 | 6/2014 | Legendre et al. |
| 8,764,693 B1 | 7/2014 | Graham et al. |
| 8,834,547 B2 | 9/2014 | Anderson et al. |
| 9,149,322 B2 | 10/2015 | Knowlton |
| 2001/0005791 A1 | 6/2001 | Ginsburg et al. |
| 2001/0007952 A1 | 7/2001 | Shimizu |
| 2001/0023364 A1 | 9/2001 | Ahn |
| 2001/0031459 A1 | 10/2001 | Fahy et al. |
| 2001/0039439 A1 | 11/2001 | Elkins et al. |
| 2001/0045104 A1 | 11/2001 | Bailey, Sr. et al. |
| 2001/0047196 A1 | 11/2001 | Ginsburg et al. |
| 2002/0026226 A1 | 2/2002 | Ein |
| 2002/0032473 A1 | 3/2002 | Kushnir et al. |
| 2002/0042607 A1 | 4/2002 | Palmer et al. |
| 2002/0049483 A1 | 4/2002 | Knowlton |
| 2002/0058975 A1 | 5/2002 | Bieberich |
| 2002/0062142 A1 | 5/2002 | Knowlton |
| 2002/0068338 A1 | 6/2002 | Nanda et al. |
| 2002/0068874 A1 | 6/2002 | Zuckerwar et al. |
| 2002/0082668 A1 | 6/2002 | Ingman |
| 2002/0103520 A1 | 8/2002 | Latham |
| 2002/0107558 A1 | 8/2002 | Clifton et al. |
| 2002/0117293 A1 | 8/2002 | Campbell |
| 2002/0120315 A1 | 8/2002 | Furuno et al. |
| 2002/0128648 A1 | 9/2002 | Weber et al. |
| 2002/0151830 A1 | 10/2002 | Kahn |
| 2002/0151887 A1 | 10/2002 | Stern et al. |
| 2002/0156509 A1 | 10/2002 | Cheung |
| 2002/0188286 A1 | 12/2002 | Quijano et al. |
| 2002/0198518 A1 | 12/2002 | Mikus et al. |
| 2003/0032900 A1 | 2/2003 | Ella |
| 2003/0044764 A1 | 3/2003 | Soane et al. |

(56) References Cited

U.S. PATENT DOCUMENTS

| | | |
|---|---|---|
| 2003/0055414 A1 | 3/2003 | Altshuler et al. |
| 2003/0062040 A1 | 4/2003 | Lurie et al. |
| 2003/0069618 A1 | 4/2003 | Smith, III et al. |
| 2003/0077326 A1 | 4/2003 | Newton et al. |
| 2003/0077329 A1 | 4/2003 | Kipp et al. |
| 2003/0079488 A1 | 5/2003 | Bieberich |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0109911 A1 | 6/2003 | Lachenbruch et al. |
| 2003/0114885 A1 | 6/2003 | Nova et al. |
| 2003/0120268 A1 | 6/2003 | Bertolero et al. |
| 2003/0125649 A1 | 7/2003 | McIntosh et al. |
| 2003/0187488 A1 | 10/2003 | Kreindel et al. |
| 2003/0199226 A1 | 10/2003 | Sommer et al. |
| 2003/0199859 A1 | 10/2003 | Altshuler et al. |
| 2003/0220594 A1 | 11/2003 | Halvorson et al. |
| 2003/0220635 A1 | 11/2003 | Knowlton et al. |
| 2003/0220674 A1 | 11/2003 | Anderson et al. |
| 2003/0236487 A1 | 12/2003 | Knowlton |
| 2004/0002705 A1 | 1/2004 | Knowlton et al. |
| 2004/0006328 A1 | 1/2004 | Anderson |
| 2004/0009936 A1 | 1/2004 | Tang et al. |
| 2004/0024437 A1 | 2/2004 | Machold et al. |
| 2004/0030332 A1 | 2/2004 | Knowlton et al. |
| 2004/0034341 A1 | 2/2004 | Altshuler et al. |
| 2004/0039312 A1 | 2/2004 | Hillstead et al. |
| 2004/0044384 A1 | 3/2004 | Leber et al. |
| 2004/0049178 A1 | 3/2004 | Abboud et al. |
| 2004/0073079 A1 | 4/2004 | Altshuler et al. |
| 2004/0074629 A1 | 4/2004 | Noel |
| 2004/0077977 A1 | 4/2004 | Ella et al. |
| 2004/0082886 A1 | 4/2004 | Timpson |
| 2004/0093042 A1 | 5/2004 | Altshuler et al. |
| 2004/0104012 A1 | 6/2004 | Zhou et al. |
| 2004/0106867 A1 | 6/2004 | Eshel et al. |
| 2004/0133251 A1 | 7/2004 | Altshuler et al. |
| 2004/0162596 A1 | 8/2004 | Altshuler et al. |
| 2004/0176667 A1 | 9/2004 | Mihai et al. |
| 2004/0186535 A1 | 9/2004 | Knowlton |
| 2004/0199226 A1 | 10/2004 | Shadduck |
| 2004/0206365 A1 | 10/2004 | Knowlton |
| 2004/0210214 A1 | 10/2004 | Knowlton |
| 2004/0210287 A1 | 10/2004 | Greene |
| 2004/0215294 A1 | 10/2004 | Littrup et al. |
| 2004/0249427 A1 | 12/2004 | Nabilsi et al. |
| 2004/0259855 A1 | 12/2004 | Anderson et al. |
| 2004/0260209 A1 | 12/2004 | Ella et al. |
| 2004/0260210 A1 | 12/2004 | Ella et al. |
| 2004/0260211 A1 | 12/2004 | Maalouf |
| 2004/0267339 A1 | 12/2004 | Yon et al. |
| 2005/0010197 A1 | 1/2005 | Lau et al. |
| 2005/0033957 A1 | 2/2005 | Enokida |
| 2005/0049526 A1 | 3/2005 | Baer |
| 2005/0049543 A1 | 3/2005 | Anderson et al. |
| 2005/0049661 A1 | 3/2005 | Koffroth |
| 2005/0113725 A1 | 5/2005 | Masuda |
| 2005/0143781 A1 | 6/2005 | Carbunaru et al. |
| 2005/0145372 A1 | 7/2005 | Noel |
| 2005/0149153 A1 | 7/2005 | Nakase et al. |
| 2005/0154314 A1 | 7/2005 | Quistgaard |
| 2005/0154431 A1 | 7/2005 | Quistgaard et al. |
| 2005/0159986 A1 | 7/2005 | Breeland et al. |
| 2005/0177075 A1 | 8/2005 | Meunier et al. |
| 2005/0182462 A1 | 8/2005 | Chornenky et al. |
| 2005/0187495 A1 | 8/2005 | Quistgaard et al. |
| 2005/0187597 A1 | 8/2005 | Vanderschuit |
| 2005/0203446 A1 | 9/2005 | Takashima |
| 2005/0215987 A1 | 9/2005 | Slatkine |
| 2005/0222565 A1 | 10/2005 | Manstein |
| 2005/0251117 A1 | 11/2005 | Anderson et al. |
| 2005/0251120 A1 | 11/2005 | Anderson et al. |
| 2005/0261753 A1 | 11/2005 | Littrup et al. |
| 2005/0277859 A1 | 12/2005 | Carlsmith et al. |
| 2005/0283144 A1 | 12/2005 | Shiono et al. |
| 2006/0030778 A1 | 2/2006 | Mendlein et al. |
| 2006/0035380 A1 | 2/2006 | Saint-Leger |
| 2006/0036300 A1 | 2/2006 | Kreindel |
| 2006/0041704 A1 | 2/2006 | Choi |
| 2006/0074313 A1 | 4/2006 | Slayton et al. |
| 2006/0079852 A1 | 4/2006 | Bubb et al. |
| 2006/0094988 A1 | 5/2006 | Tosaya et al. |
| 2006/0106836 A1 | 5/2006 | Masugi et al. |
| 2006/0111613 A1 | 5/2006 | Boutillette et al. |
| 2006/0122509 A1 | 6/2006 | Desilets |
| 2006/0189964 A1 | 8/2006 | Anderson et al. |
| 2006/0195168 A1 | 8/2006 | Dunbar et al. |
| 2006/0200063 A1 | 9/2006 | Munro et al. |
| 2006/0206040 A1 | 9/2006 | Greenberg et al. |
| 2006/0206110 A1 | 9/2006 | Knowlton et al. |
| 2006/0234899 A1 | 10/2006 | Nekmard et al. |
| 2006/0259102 A1 | 11/2006 | Slatkine |
| 2006/0265032 A1 | 11/2006 | Hennings et al. |
| 2006/0270745 A1 | 11/2006 | Hunt et al. |
| 2006/0293734 A1 | 12/2006 | Scott et al. |
| 2007/0010811 A1 | 1/2007 | Stern et al. |
| 2007/0010861 A1 | 1/2007 | Anderson et al. |
| 2007/0032561 A1 | 2/2007 | Lin et al. |
| 2007/0038156 A1 | 2/2007 | Rosenberg |
| 2007/0055156 A1 | 3/2007 | Desilets et al. |
| 2007/0055173 A1 | 3/2007 | DeLonzor et al. |
| 2007/0055179 A1 | 3/2007 | Deem et al. |
| 2007/0055180 A1 | 3/2007 | Deem et al. |
| 2007/0055181 A1 | 3/2007 | Deem et al. |
| 2007/0073367 A1 | 3/2007 | Jones et al. |
| 2007/0078502 A1 | 4/2007 | Weber et al. |
| 2007/0100398 A1 | 5/2007 | Sloan |
| 2007/0106342 A1 | 5/2007 | Schumann |
| 2007/0129714 A1 | 6/2007 | Elkins et al. |
| 2007/0135876 A1 | 6/2007 | Weber |
| 2007/0141265 A1 | 6/2007 | Thomson |
| 2007/0179482 A1 | 8/2007 | Anderson |
| 2007/0198071 A1 | 8/2007 | Ting et al. |
| 2007/0219540 A1 | 9/2007 | Masotti et al. |
| 2007/0239075 A1 | 10/2007 | Rosenberg et al. |
| 2007/0239150 A1 | 10/2007 | Zvuloni et al. |
| 2007/0249519 A1 | 10/2007 | Guha et al. |
| 2007/0255187 A1 | 11/2007 | Branch |
| 2007/0255274 A1 | 11/2007 | Stern et al. |
| 2007/0255362 A1 | 11/2007 | Levinson et al. |
| 2007/0265585 A1 | 11/2007 | Joshi et al. |
| 2007/0265614 A1 | 11/2007 | Stern et al. |
| 2007/0270925 A1 | 11/2007 | Levinson |
| 2007/0282249 A1 | 12/2007 | Quisenberry et al. |
| 2007/0282318 A1 | 12/2007 | Spooner et al. |
| 2008/0014627 A1 | 1/2008 | Merchant et al. |
| 2008/0046047 A1 | 2/2008 | Jacobs |
| 2008/0058784 A1 | 3/2008 | Manstein et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0097207 A1 | 4/2008 | Cai et al. |
| 2008/0139901 A1 | 6/2008 | Altshuler et al. |
| 2008/0140061 A1 | 6/2008 | Toubia et al. |
| 2008/0140371 A1 | 6/2008 | Warner |
| 2008/0161892 A1 | 7/2008 | Mercuro et al. |
| 2008/0183164 A1 | 7/2008 | Elkins et al. |
| 2008/0188915 A1 | 8/2008 | Mills et al. |
| 2008/0248554 A1 | 10/2008 | Merchant et al. |
| 2008/0269851 A1 | 10/2008 | Deem et al. |
| 2008/0287839 A1 | 11/2008 | Rosen et al. |
| 2008/0300529 A1 | 12/2008 | Reinstein |
| 2008/0312651 A1 | 12/2008 | Pope et al. |
| 2009/0012434 A1 | 1/2009 | Anderson |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0024023 A1 | 1/2009 | Welches et al. |
| 2009/0076488 A1 | 3/2009 | Welches et al. |
| 2009/0112134 A1 | 4/2009 | Avni |
| 2009/0118722 A1 | 5/2009 | Ebbers et al. |
| 2009/0149929 A1 | 6/2009 | Levinson et al. |

(56) References Cited

U.S. PATENT DOCUMENTS

| | | |
|---|---|---|
| 2009/0149930 A1 | 6/2009 | Schenck |
| 2009/0171253 A1 | 7/2009 | Davenport |
| 2009/0171334 A1 | 7/2009 | Elkins et al. |
| 2009/0221938 A1 | 9/2009 | Rosenberg et al. |
| 2009/0226424 A1 | 9/2009 | Hsu |
| 2009/0276018 A1 | 11/2009 | Brader |
| 2009/0281464 A1 | 11/2009 | Cioanta et al. |
| 2009/0299234 A1 | 12/2009 | Cho et al. |
| 2009/0306749 A1 | 12/2009 | Mulindwa |
| 2009/0312676 A1 | 12/2009 | Rousso et al. |
| 2009/0312693 A1 | 12/2009 | Thapliyal et al. |
| 2009/0326621 A1 | 12/2009 | El-Galley |
| 2010/0015190 A1 | 1/2010 | Hassler |
| 2010/0028969 A1 | 2/2010 | Mueller et al. |
| 2010/0030306 A1 | 2/2010 | Edelman et al. |
| 2010/0036295 A1 | 2/2010 | Altshuler et al. |
| 2010/0042087 A1 | 2/2010 | Goldboss et al. |
| 2010/0049178 A1 | 2/2010 | Deem et al. |
| 2010/0081971 A1 | 4/2010 | Allison |
| 2010/0087806 A1 | 4/2010 | Da Silva et al. |
| 2010/0152824 A1 | 6/2010 | Allison |
| 2010/0168726 A1 | 7/2010 | Brookman |
| 2010/0179531 A1 | 7/2010 | Nebrigic et al. |
| 2010/0198064 A1 | 8/2010 | Perl et al. |
| 2010/0217349 A1 | 8/2010 | Fahey et al. |
| 2010/0241023 A1 | 9/2010 | Gilbert |
| 2010/0268220 A1 | 10/2010 | Johnson et al. |
| 2010/0280582 A1 | 11/2010 | Baker et al. |
| 2011/0009860 A1 | 1/2011 | Chornenky et al. |
| 2011/0040235 A1 | 2/2011 | Castel |
| 2011/0040299 A1 | 2/2011 | Kim et al. |
| 2011/0046523 A1 | 2/2011 | Altshuler et al. |
| 2011/0060323 A1 | 3/2011 | Baust et al. |
| 2011/0066083 A1 | 3/2011 | Tosaya et al. |
| 2011/0066216 A1 | 3/2011 | Ting et al. |
| 2011/0077557 A1 | 3/2011 | Wing et al. |
| 2011/0077723 A1 | 3/2011 | Parish et al. |
| 2011/0112405 A1 | 5/2011 | Barthe et al. |
| 2011/0112520 A1 | 5/2011 | Kreindel |
| 2011/0144631 A1 | 6/2011 | Elkins et al. |
| 2011/0152849 A1 | 6/2011 | Baust et al. |
| 2011/0172651 A1 | 7/2011 | Altshuler et al. |
| 2011/0189129 A1 | 8/2011 | Qiu et al. |
| 2011/0196395 A1 | 8/2011 | Maschke |
| 2011/0196438 A1 | 8/2011 | Mnozil et al. |
| 2011/0202048 A1 | 8/2011 | Nebrigic et al. |
| 2011/0238050 A1 | 9/2011 | Allison et al. |
| 2011/0238051 A1 | 9/2011 | Levinson et al. |
| 2011/0257642 A1 | 10/2011 | Griggs, III |
| 2011/0288537 A1 | 11/2011 | Halaka |
| 2011/0300079 A1 | 12/2011 | Martens et al. |
| 2011/0301585 A1 | 12/2011 | Goulko |
| 2011/0313411 A1 | 12/2011 | Anderson et al. |
| 2011/0313412 A1 | 12/2011 | Kim et al. |
| 2012/0010609 A1 | 1/2012 | Deem et al. |
| 2012/0016239 A1 | 1/2012 | Barthe et al. |
| 2012/0022518 A1 | 1/2012 | Levinson |
| 2012/0022622 A1 | 1/2012 | Johnson et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0065629 A1 | 3/2012 | Elkins et al. |
| 2012/0083862 A1 | 4/2012 | Altshuler et al. |
| 2012/0101549 A1 | 4/2012 | Schumann |
| 2012/0109041 A1 | 5/2012 | Munz |
| 2012/0158100 A1 | 6/2012 | Schomacker |
| 2012/0209363 A1 | 8/2012 | Williams, III et al. |
| 2012/0233736 A1 | 9/2012 | Tepper et al. |
| 2012/0239123 A1 | 9/2012 | Weber et al. |
| 2012/0253416 A1 | 10/2012 | Erez et al. |
| 2012/0259322 A1 | 10/2012 | Fourkas et al. |
| 2012/0277674 A1 | 11/2012 | Clark, III et al. |
| 2012/0310232 A1 | 12/2012 | Erez |
| 2013/0018236 A1 | 1/2013 | Altshuler et al. |
| 2013/0019374 A1 | 1/2013 | Schwartz |
| 2013/0066309 A1 | 3/2013 | Levinson |
| 2013/0073017 A1 | 3/2013 | Liu et al. |
| 2013/0079684 A1 | 3/2013 | Rosen et al. |
| 2013/0116758 A1 | 5/2013 | Levinson et al. |
| 2013/0116759 A1 | 5/2013 | Levinson et al. |
| 2013/0150844 A1 | 6/2013 | Deem et al. |
| 2013/0158440 A1 | 6/2013 | Allison |
| 2013/0158636 A1 | 6/2013 | Ting et al. |
| 2013/0166003 A1 | 6/2013 | Johnson et al. |
| 2013/0190744 A1 | 7/2013 | Avram et al. |
| 2013/0238062 A1 | 9/2013 | Edoute et al. |
| 2013/0245507 A1 | 9/2013 | Khorassani |
| 2013/0253384 A1 | 9/2013 | Anderson et al. |
| 2013/0253493 A1 | 9/2013 | Anderson et al. |
| 2013/0253494 A1 | 9/2013 | Anderson et al. |
| 2013/0253495 A1 | 9/2013 | Anderson et al. |
| 2013/0253496 A1 | 9/2013 | Anderson et al. |
| 2013/0303904 A1 | 11/2013 | Barthe et al. |
| 2013/0303905 A1 | 11/2013 | Barthe et al. |
| 2013/0331914 A1 | 12/2013 | Lee et al. |
| 2014/0005759 A1 | 1/2014 | Fahey et al. |
| 2014/0005760 A1 | 1/2014 | Levinson et al. |
| 2014/0067025 A1 | 3/2014 | Levinson et al. |
| 2014/0142469 A1 | 5/2014 | Britva et al. |
| 2014/0200487 A1 | 7/2014 | Ramdas et al. |
| 2014/0200488 A1 | 7/2014 | Seo et al. |
| 2014/0222121 A1 | 8/2014 | Spence et al. |
| 2014/0277219 A1 | 9/2014 | Nanda |
| 2014/0277302 A1 | 9/2014 | Weber et al. |
| 2014/0277303 A1 | 9/2014 | Biser et al. |
| 2014/0303697 A1 | 10/2014 | Anderson et al. |
| 2015/0209174 A1 | 7/2015 | Abreu |
| 2015/0216719 A1* | 8/2015 | DeBenedictis ......... A61F 7/007 601/2 |
| 2015/0216720 A1 | 8/2015 | DeBenedictis et al. |
| 2015/0216816 A1 | 8/2015 | O'Neil et al. |
| 2015/0223975 A1 | 8/2015 | Anderson et al. |
| 2015/0283022 A1 | 10/2015 | Lee et al. |
| 2015/0328077 A1 | 11/2015 | Levinson |
| 2015/0335468 A1 | 11/2015 | Rose et al. |
| 2015/0342780 A1 | 12/2015 | Levinson et al. |
| 2016/0051308 A1 | 2/2016 | Pennybacker et al. |
| 2016/0051401 A1 | 2/2016 | Yee et al. |
| 2016/0135985 A1 | 5/2016 | Anderson |
| 2016/0324684 A1 | 11/2016 | Levinson et al. |
| 2017/0007309 A1 | 1/2017 | DeBenedictis et al. |
| 2017/0079833 A1 | 3/2017 | Frangineas, Jr. et al. |
| 2017/0105869 A1 | 4/2017 | Frangineas, Jr. et al. |
| 2017/0165105 A1 | 6/2017 | Anderson et al. |
| 2017/0196731 A1 | 7/2017 | DeBenedictis et al. |
| 2017/0239079 A1 | 8/2017 | Root et al. |
| 2017/0325992 A1 | 11/2017 | DeBenedictis et al. |
| 2017/0325993 A1 | 11/2017 | Lozano et al. |
| 2017/0326042 A1 | 11/2017 | Zeng et al. |
| 2017/0326346 A1 | 11/2017 | Lozano et al. |
| 2018/0185081 A1 | 7/2018 | O'neil et al. |
| 2018/0185189 A1 | 7/2018 | Weber et al. |
| 2018/0263677 A1 | 9/2018 | Hilton et al. |
| 2018/0271767 A1 | 9/2018 | Lozano et al. |
| 2018/0310950 A1 | 11/2018 | Yee et al. |

FOREIGN PATENT DOCUMENTS

| | | |
|---|---|---|
| CA | 2585214 A1 | 10/2007 |
| CH | 333982 A | 11/1958 |
| CN | 86200604 U | 10/1987 |
| CN | 2514795 Y | 10/2002 |
| CN | 2514811 Y | 10/2002 |
| CN | 1511503 A | 7/2004 |
| CN | 1741777 A | 3/2006 |
| CN | 1817990 A | 8/2006 |
| CN | 2843367 Y | 12/2006 |
| CN | 2850584 Y | 12/2006 |
| CN | 2850585 Y | 12/2006 |
| CN | 200970265 Y | 11/2007 |
| CN | 101259329 A | 9/2008 |
| CN | 101309657 A | 11/2008 |
| DE | 532976 C | 9/1931 |

(56) References Cited

FOREIGN PATENT DOCUMENTS

| | | |
|---|---|---|
| DE | 2851602 A1 | 6/1980 |
| DE | 4213584 A1 | 11/1992 |
| DE | 4224595 A1 | 1/1994 |
| DE | 4238291 A1 | 5/1994 |
| DE | 4445627 A1 | 6/1996 |
| DE | 19800416 A1 | 7/1999 |
| EP | 263069 A2 | 4/1988 |
| EP | 0397043 A1 | 11/1990 |
| EP | 0406244 A1 | 1/1991 |
| EP | 560309 A1 | 9/1993 |
| EP | 0598824 A1 | 6/1994 |
| EP | 1030611 A1 | 8/2000 |
| EP | 1201266 A1 | 5/2002 |
| EP | 1568395 A1 | 8/2005 |
| EP | 2260801 A2 | 12/2010 |
| EP | 2289598 A1 | 3/2011 |
| EP | 2527005 A1 | 11/2012 |
| FR | 854937 A | 4/1940 |
| FR | 2744358 A1 | 8/1997 |
| FR | 2745935 A1 | 9/1997 |
| FR | 2767476 A1 | 2/1999 |
| FR | 2776920 A1 | 10/1999 |
| FR | 2789893 A1 | 8/2000 |
| FR | 2805989 A1 | 9/2001 |
| GB | 387960 A | 2/1933 |
| GB | 2120944 A | 12/1983 |
| GB | 2202447 A | 9/1988 |
| GB | 2248183 A | 4/1992 |
| GB | 2263872 A | 8/1993 |
| GB | 2286660 A | 8/1995 |
| GB | 2323659 A | 9/1998 |
| JP | 58187454 A | 11/1983 |
| JP | S6094113 U | 6/1985 |
| JP | 62082977 A | 4/1987 |
| JP | 63076895 A | 4/1988 |
| JP | 01223961 A | 9/1989 |
| JP | 03051964 A | 3/1991 |
| JP | 03259975 A | 11/1991 |
| JP | 04093597 A | 3/1992 |
| JP | 06261933 A | 9/1994 |
| JP | 07194666 A | 8/1995 |
| JP | 07268274 A | 10/1995 |
| JP | 09164163 A | 6/1997 |
| JP | 10216169 A | 8/1998 |
| JP | 10223961 A | 8/1998 |
| JP | 2000503154 A | 3/2000 |
| JP | 3065657 B2 | 7/2000 |
| JP | 2001046416 A | 2/2001 |
| JP | 2002125993 A | 5/2002 |
| JP | 2002224051 A | 8/2002 |
| JP | 2002282295 A | 10/2002 |
| JP | 2002290397 A | 10/2002 |
| JP | 2002543668 A | 12/2002 |
| JP | 2003190201 A | 7/2003 |
| JP | 2004013600 A | 1/2004 |
| JP | 2004073812 A | 3/2004 |
| JP | 2004159666 A | 6/2004 |
| JP | 2005039790 A | 2/2005 |
| JP | 2005065984 A | 3/2005 |
| JP | 2005110755 A | 4/2005 |
| JP | 2005509977 A | 4/2005 |
| JP | 3655820 B2 | 6/2005 |
| JP | 2005520608 A | 7/2005 |
| JP | 2005237908 A | 9/2005 |
| JP | 2005323716 A | 11/2005 |
| JP | 2006026001 A | 2/2006 |
| JP | 2006130055 A | 5/2006 |
| JP | 2006520949 A | 9/2006 |
| JP | 2007270459 A | 10/2007 |
| JP | 2008532591 A | 8/2008 |
| JP | 2009515232 A | 4/2009 |
| JP | 2009189757 A | 8/2009 |
| KR | 200173222 Y1 | 12/1999 |
| KR | 1020040094508 A | 11/2004 |
| KR | 20090000258 U | 1/2009 |
| KR | 1020130043299 A | 4/2013 |
| KR | 1020140038165 A | 3/2014 |
| RU | 2036667 C1 | 6/1995 |
| SU | 532976 A1 | 11/1978 |
| TW | 0476644 B | 2/2002 |
| WO | 8503216 A1 | 8/1985 |
| WO | 9114417 A1 | 10/1991 |
| WO | 9404116 A1 | 3/1994 |
| WO | 9623447 A1 | 8/1996 |
| WO | 9626693 A1 | 9/1996 |
| WO | 9636293 A1 | 11/1996 |
| WO | 9637158 A1 | 11/1996 |
| WO | 9704832 A1 | 2/1997 |
| WO | 9705828 A1 | 2/1997 |
| WO | 9722262 A2 | 6/1997 |
| WO | 9724088 A1 | 7/1997 |
| WO | 9725798 A1 | 7/1997 |
| WO | 9748440 A1 | 12/1997 |
| WO | 9829134 A2 | 7/1998 |
| WO | 9831321 A1 | 7/1998 |
| WO | 9841156 A1 | 9/1998 |
| WO | 9841157 A1 | 9/1998 |
| WO | 9909928 A1 | 3/1999 |
| WO | 9916502 A1 | 4/1999 |
| WO | 9938469 A1 | 8/1999 |
| WO | 9949937 A1 | 10/1999 |
| WO | 0044346 A1 | 8/2000 |
| WO | 0044349 A1 | 8/2000 |
| WO | 0065770 A1 | 11/2000 |
| WO | 0067685 A1 | 11/2000 |
| WO | 0100269 A1 | 1/2001 |
| WO | 0113989 A1 | 3/2001 |
| WO | 0114012 A1 | 3/2001 |
| WO | 0134048 A1 | 5/2001 |
| WO | 0205736 A1 | 1/2002 |
| WO | 02102921 A1 | 12/2002 |
| WO | 03007859 A1 | 1/2003 |
| WO | 03078596 A2 | 9/2003 |
| WO | 03079916 A1 | 10/2003 |
| WO | 2004000098 A2 | 12/2003 |
| WO | 2004080279 A2 | 9/2004 |
| WO | 2004090939 A2 | 10/2004 |
| WO | 2005033957 A1 | 4/2005 |
| WO | 2005046540 A1 | 5/2005 |
| WO | 2005060354 A2 | 7/2005 |
| WO | 2005096979 A1 | 10/2005 |
| WO | 2005112815 A1 | 12/2005 |
| WO | 2006066226 A1 | 6/2006 |
| WO | 2006094348 A1 | 9/2006 |
| WO | 2006106836 A1 | 10/2006 |
| WO | 2006116603 A2 | 11/2006 |
| WO | 2006127467 A2 | 11/2006 |
| WO | 2007012083 A2 | 1/2007 |
| WO | 2007028975 A1 | 3/2007 |
| WO | 2007041642 A2 | 4/2007 |
| WO | 2007101039 A1 | 9/2007 |
| WO | 2007127924 A2 | 11/2007 |
| WO | 2007145421 A1 | 12/2007 |
| WO | 2007145422 A1 | 12/2007 |
| WO | 2008006018 A2 | 1/2008 |
| WO | 2008039556 A1 | 4/2008 |
| WO | 2008039557 A1 | 4/2008 |
| WO | 2008055243 A2 | 5/2008 |
| WO | 2008143678 A1 | 11/2008 |
| WO | 2009011708 A1 | 1/2009 |
| WO | 2009026471 A1 | 2/2009 |
| WO | 2010077841 A1 | 7/2010 |
| WO | 2010127315 A2 | 11/2010 |
| WO | 2012012296 A1 | 1/2012 |
| WO | 2012103242 A1 | 8/2012 |
| WO | 2013013059 A1 | 1/2013 |
| WO | 2013075006 A1 | 5/2013 |
| WO | 2013075016 A1 | 5/2013 |
| WO | WO 2013/075006 A1 * 5/2013 | ............... A61F 7/00 |
| WO | 2013190337 A1 | 12/2013 |
| WO | 2014151872 A3 | 9/2014 |
| WO | 2014191263 A1 | 12/2014 |
| WO | 2015117001 A1 | 8/2015 |
| WO | 2015117005 A1 | 8/2015 |

(56) References Cited

FOREIGN PATENT DOCUMENTS

| WO | 2015117026 A2 | 8/2015 |
|---|---|---|
| WO | 2015117032 A1 | 8/2015 |
| WO | 2015117036 A2 | 8/2015 |
| WO | 2016028796 A1 | 2/2016 |
| WO | 2016048721 A1 | 3/2016 |

OTHER PUBLICATIONS

Aguilar et al., "Modeling Cryogenic Spray Temperature and Evaporation Rate Based on Single-Droplet Analysis," Eighth International Conference on Liquid Atomization and Spray Systems, Pasadena, CA, USA, Jul. 2000, 7 pages.

Al-Sakere, B. et al. "Tumor Ablation with Irreversible Electroporation," PLoS One, Issue 11, Nov. 2007, 8 pages.

Alster, T. et al., "Cellulite Treatment Using a Novel Combination Radiofrequency, Infrared Light, and Mechanical Tissue Manipulation Device," Journal of Cosmetic and Laser Therapy, vol. 7, 2005, pp. 81-85.

Ardevol, A. et al., "Cooling Rates of Tissue Samples During Freezing with Liquid Nitrogen," Journal of Biochemical and Biophysical Methods, vol. 27, 1993, pp. 77-86.

Arena, C. B. et al., "High-Frequency Irreversible Electroporation (H-FIRE) for Non-Thermal Ablation Without Muscle Contraction," BioMedical Engineering OnLine 2011, 10:102, Nov. 21, 2011, 21 pgs.

Becker, S. M. et al. "Local Temperature Rises Influence In Vivo Electroporation Pore Development: A Numerical Stratum Corneum Lipid Phase Transition Model," Journal of Biomechanical Engineering, vol. 129, Oct. 2007, pp. 712-721.

Bohm, T. et al., "Saline-Enhanced Radiofrequency Ablation of Breast Tissue: an in Vitro Feasibility Study," Investigative Radiology, vol. 35 (3), 2000, pp. 149-157.

Bondei, E. et al., "Disorders of Subcutaneous Tissue (Cold Panniculitis)," Dermatology in General Medicine, Fourth Edition, vol. 1, Chapter 108, 1993, Section 16, pp. 1333-1334.

Burge, S.M. et al., "Hair Follicle Destruction and Regeneration in Guinea Pig Skin after Cutaneous Freeze Injury," Cryobiology, 27(2), 1990, pp. 153-163.

Coban, Y. K. et al., "Ischemia-Reperfusion Injury of Adipofascial Tissue: An Experimental Study Evaluating Early Histologic and Biochemical Alterations in Rats," Mediators of Inflammation, 2005, 5, pp. 304-308.

Del Pino, M. E. et al. "Effect of Controlled Volumetric Tissue Heating with Radiofrequency on Cellulite and the Subcutaneous Tissue of the Buttocks and Thighs," Journal of Drugs in Dermatology, vol. 5, Issue 8, Sep. 2006, pp. 714-722.

Donski, P. K. et al., "The Effects of Cooling no Experimental Free Flap Survival," British Journal of Plastic Surgery, vol. 33, 1980, pp. 353-360.

Duck, F. A., Physical Properties of Tissue, Academic Press Ltd., chapters 4 & 5, 1990, pp. 73-165.

Duncan, W. C. et al., "Cold Panniculitis," Archives of Dermatology, vol. 94, Issue 6, Dec. 1966, pp. 722-724.

Epstein, E. H. et al., "Popsicle Panniculitis," The New England Journal of Medicine, 282(17), Apr. 23, 1970, pp. 966-967.

Fournier, L. et al. "Lattice Model for the Kinetics of Rupture of Fluid Bilayer Membranes," Physical Review, vol. 67, 2003, pp. 051908-1-051908-11.

Gabriel, S. et al., "The Dielectric Properties of Biological Tissues: II. Measurements in the Frequency Range 10 Hz to 20 GHz," Physics in Medicine and Biology, vol. 41, 1996, pp. 2251-2269.

Gage, A. "Current Progress in Cryosurgery," Cryobiology 25, 1988, pp. 483-486.

Gatto, H. "Effects of Thermal Shocks on Interleukin-1 Levels and Heat Shock Protein 72 (HSP72) Expression in Normal Human Keratinocytes," PubMed, Archives of Dermatological Research, vol. 284, Issue 7, 1992: pp. 414-417 [Abstract].

Hale, H. B. et al., "Influence of Chronic Heat Exposure and Prolonged Food Deprivation on Excretion of Magnesium, Phosphorus, Calcium, Hydrogen Ion & Ketones," Aerospace Medicine, vol. 39—No. 9, Sep. 1968, pp. 919-926.

Heller Page, E. et al., "Temperature-dependent skin disorders," Journal of the American Academy of Dermatology, vol. 18, No. 5, Pt 1, May 1988, pp. 1003-1019.

Hemmingsson, A. et al. "Attenuation in Human Muscle and Fat Tissue in Vivo and in Vitro," Acra Radiologica Diagnosis, vol. 23, No. 2, 1982, pp. 149-151.

Henry, F. et al., "Les Dermatoses Hivernales," Rev Med Liege, 54:11, 1999, pp. 864-866. [Abstract Attached].

Hernan, P. et al., "Study for the evaluation of the efficacy of Lipocryolysis (EEEL)", Nov. 30, 2011.

Hernan, R. P., "A Study to Evaluate the Action of Lipocryolysis", 33(3) CryoLellers, 2012, pp. 176-180.

Holland, DB. et al. "Cold shock induces the synthesis of stress proteins in human keratinocytes," PubMed Journal of Investigative Dermatology; 101(2): Aug. 1993, pp. 196-199.

Holman, W. L. et al., "Variation in Cryolesion Penetration Due to Probe Size and Tissue Thermal Conductivity," The Annals of Thoracic Surgery, vol. 53, 1992, pp. 123-126.

Hong, J.S. et al., "Patterns of Ice Formation in Normal and Malignant Breast Tissue," Cryobiology 31, 1994, pp. 109-120.

Huang et al. "Comparative Proteomic Profiling of Murine Skin," Journal of Investigative Dermatology, vol. 121(1), Jul. 2003, pp. 51-64.

Isambert, H. "Understanding the Electroporation of Cells and Artificial Bilayer Membranes," Physical Review Letters, vol. 80, No. 15, 1998, pp. 3404-3707.

International Searching Authority, "International Search Report and Written Opinion," PCT/US2015/013971, dated Jul. 16, 2015., 18 pages.

International Searching Authority, "International Preliminary Report on Patentability," PCT/US2015/013971, dated Aug. 11, 2016., 12 pages.

Jalian, H. R. et al., "Cryolipolysis: A Historical Perspective and Current Clinical Practice", 32(1) Semin. Cutan. Med. Surg., 2013, pp. 31-34.

Kellum, R. E. et al., "Sclerema Neonatorum: Report of Case and Analysis of Subcutaneous and Epidermal-Dermal Lipids by Chromatographic Methods," Archives of Dermatology, vol. 97, Apr. 1968, pp. 372-380.

Koska, J. et al., "Endocrine Regulation of Subcutaneous Fat Metabolism During Cold Exposure in Humans," Annals of the New York Academy of Sciences, vol. 967, 2002,pp. 500-505.

Kundu, S. K. et al., "Breath Acetone Analyzer: Diagnostic Tool to Monitor Dietary Fat Loss," Clinical Chemistry, vol. 39, Issue (1), 1993, pp. 87-92.

Kundu, S. K. et al., "Novel Solid-Phase Assay of Ketone Bodies in Urine," Clinical Chemistry, vol. 37, Issue (9), 1991, pp. 1565-1569.

Kuroda, S. et al. "Thermal Distribution of Radio-Frequency Inductive Hyperthermia Using an Inductive Aperture-Type Applicator: Evaluation of the Effect of Tumor Size and Depth", Medical and Biological Engineering and Computing, vol. 37, 1999, pp. 285-290.

Laugier, P. et al., "In Vivo Results with a New Device for Ultrasonic Monitoring of Pig Skin Cryosurgery: The Echographic Cryprobe," The Society for Investigative Dermatology, Inc., vol. 111, No. 2, Aug. 1998, pp. 314-319.

Levchenko et al., "Effect of Dehydration on Lipid Metabolism" Ukrainskii Biokhimicheskii Zhurnal, vol. 50, Issue 1, 1978, pp. 95-97.

Lidagoster, MD et al., "Comparison of Autologous Fat Transfer in Fresh, Refrigerated, and Frozen Specimens: An Animal Model," Annals of Plastic Surgery, vol. 44, No. 5, May 2000, pp. 512-515.

Liu, A. Y.-C. et al., "Transient Cold Shock Induces the Heat Shock Response upon Recovery at 37 C in Human Cells," Journal of Biological Chemistry 269(20), May 20, 1994, pp. 14768-14775.

L'Vova, S.P. "Lipid Levels and Lipid Peroxidation in Frog Tissues During Hypothermia and Hibernation" Ukrainskii Biokhimicheskii Zhurnal, vol. 62, Issue 1, 1990, pp. 65-70.

Maize, J.C. "Panniculitis," Cutaneous Pathology, Chapter 13, 1998, 327-344.

(56) References Cited

OTHER PUBLICATIONS

Malcolm, G. T. et al., "Fatty Acid Composition of Adipose Tissue in Humans: Differences between Subcutaneous Sites," The American Journal of Clinical Nutrition, vol. 50, 1989, pp. 288-291.
Manstein, D. et al. "A Novel Cryotherapy Method of Non-invasive, Selective Lipolysis," LasersSurg.Med 40:S20, 2008, p. 104.
Manstein, D. et al. "Selective Cryolysis: a Novel Method of Non-Invasive Fat Removal," Lasers in Surgery and Medicine: The Official Journal of the ASLMS, vol. 40, No. 9, Nov. 2008, pp. 595-604.
Mayoral, "Case Reports: Skin Tightening with a Combined Unipolar and Bipolar Radiofrequency Device," Journal of Drugs in Dermatology, 2007, pp. 212-215.
Mazur, P. "Cryobiology: the Freezing of Biological Systems," Science, 68, 1970, pp. 939-949.
Merrill, T. "A Chill to the Heart: A System to Deliver Local Hypothermia Could One Day Improve the Lives of Heart-Attack Patients," Mechanical Engineering Magazine, Oct. 2010, 10 pages.
Miklavcic, D. et al. "Electroporation-Based Technologies and Treatments," The Journal of Membrane Biology (2010) 236:1-2, 2 pgs.
Moschella, S. L. et al., "Diseases of the Subcutaneous Tissue," in Dermatology, Second Edition, vol. 2, 1985 Chapter 19, Section II (W.B. Saunders Company, 1980) pp. 1169-1181.
Murphy, J. V. et al., "Frostbite: Pathogenesis and Treatment" The Journal of Trauma: Injury, Infection, and Critical Care, vol. 48, No. 1, Jan. 2000, pp. 171-178.
Nagao, T. et al., "Dietary Diacylglycerol Suppresses Accumulation of Body Fat Compared to Triacylglycerol in Men a Double-Blind Controlled Trial," The Journal of Nutrition, vol. 130, Issue (4), 2000, pp. 792-797.
Nagle, W. A. et al. "Cultured Chinese Hamster Cells Undergo Apoptosis After Exposure to Cold but Nonfreezing Temperatures," Cryobiology 27, 1990, pp. 439-451.
Nagore, E. et al., "Lipoatrophia Semicircularis-a Traumatic Panniculitis: Report of Seven Cases and Review of the Literature," Journal of the American Academy of Dermatology, vol. 39, Nov. 1998, pp. 879-881.
Nanda, G.S. et al., "Studies on electroporation of thermally and chemically treated human erythrocytes," Bioelectrochemistry and Bioenergetics, 34, 1994, pp. 129-134, 6 pgs.
Narins, D.J. et al. "Non-Surgical Radiofrequency Facelift", The Journal of Drugs in Dermatology, vol. 2, Issue 5, 2003, pp. 495-500.
Nielsen, B. "Thermoregulation in Rest and Exercise," Acta Physiologica Scandinavica Supplementum, vol. 323 (Copenhagen 1969), pp. 7-74.
Nishikawa, H. et al. "Ultrastructural Changes and Lipid Peroxidation in Rat Adipomusculocutaneous Flap Isotransplants after Normothermic Storage and Reperfusion," Transplantation, vol. 54, No. 5,1992, pp. 795-801.
Nurnberger, F. "So-Called Cellulite: An Invented Disease," Journal of Dermatologic Surgery and Oncology, Mar. 1978, pp. 221-229.
Pease, G. R. et al., "An Integrated Probe for Magnetic Resonance Imaging Monitored Skin Cryosurgery," Journal of Biomedical Engineering, vol. 117, Feb. 1995, pp. 59-63.
Pech, P. et al., "Attenuation Values, Volume Changes and Artifacts in Tissue Due to Freezing," Acta Radiologica ,vol. 28, Issue 6, 1987, pp. 779-782.
Peterson, L. J. et al., "Bilateral Fat Necrosis of the Scrotum," Journal of Urology, vol. 116, 1976, pp. 825-826.
Phinney, S. D. et al., "Human Subcutaneous Adipose Tissue Shows Site-Specific Differences in Fatty Acid Composition," The American Journal of Clinical Nutrition, vol. 60, 1994, pp. 725-729.
Pierard, G.E. et al., "Cellulite: From Standing Fat Herniation to Hypodermal Stretch Marks," The American Journal of Dermatology, vol. 22, Issue 1, 2000, pp. 34-37, [Abstract].
Pope, K. et al. "Selective Fibrous Septae Heating: An Additional Mechanism of Action for Capacitively Coupled Monopolar Radiofrequency" Thermage, Inc. Article, Feb. 2005, 6pgs.
Quinn, P. J. "A Lipid-Phase Separation Model of Low-Temperature Damage to Biological Membranes," Cryobiology, 22, 1985, 128-146.
Rabi, T. et al., "Metabolic Adaptations in Brown Adipose Tissue of the Hamster in Extreme Ambient Temperatures," American Journal of Physiology, vol. 231, Issue 1, Jul. 1976, pp. 153-160.
Renold, A.E. et al. "Adipose Tissue" in Handbook of Physiology, Chapter 15, (Washington, D.C., 1965) pp. 169-176.
Rossi, A. B. R. et al. "Cellulite: a Review," European Academy of Dermatology and Venercology, 2000, pp. 251-262, 12 pgs.
Rubinsky, B. "Principles of Low Temperature Cell Preservation," Heart Failure Reviews, vol. 8, 2003, pp. 277-284.
Rubinsky, B. et al., "Cryosurgery: Advances in the Application of low Temperatures to Medicine," International Journal of Refrigeration, vol. 14, Jul. 1991, pp. 190-199.
Saleh, K.Y. et al., "Two-Dimensional Ultrasound Phased Array Design for Tissue Ablation for Treatment of Benign Prostatic Hyperplasia," International Journal of Hyperthermia, vol. 20, No. 1, Feb. 2004, pp. 7-31.
Schoning, P. et al., "Experimental Frostbite: Freezing Times, Rewarming Times, and Lowest Temperatures of Pig Skin Exposed to Chilled Air," Cryobiology 27, 1990, pp. 189-193.
Shephard, R. J. "Adaptation to Exercise in the Cold," Sports Medicine, vol. 2, 1985, pp. 59-71.
Sigma-Aldrich "Poly(ethylene glycol) and Poly(ethylene oxide)," http://www.sigmaaldrich.com/materials-science/materialscience-;products.htmi?TablePage=20204110, accessed Oct. 19, 2012.
Smalls, L. K. et al. "Quantitative Model of Cellulite: Three Dimensional Skin Surface Topography, Biophysical Characterization, and Relationship to Human Perception," International Journal of Cosmetic Science, vol. 27, Issue 5, Oct. 2005, 17 pgs.
Thermage, News Release, "Study Published in Facial Plastic Surgery Journal Finds Selective Heating of Fibrous Septae Key to Success and Safety of Thermage ThermaCool System," Jun. 20, 2005, 2 pages.
Vallerand et al. "Cold Stress Increases Lipolysis, FFA Ra and TG/FFA Cycling in Humans," Aviation, Space, and Environmental Medicine 70(1), 1999, pp. 42-50.
Wang, X. et al., "Cryopreservation of Cell/Hydrogel Constructs Based on a new Cell-Assembling Technique," Sep. 5, 2009, 40 pages.
Wharton, D. A. et al., "Cold Acclimation and Cryoprotectants in a Freeze-Tolerant Antarctic Nematode, Panagrolaimus Davidi,", Journal of Comparative Physiology, vol. 170, No. 4, Mar. 2000, 2 pages.
Winkler, C. et al., "Gene Transfer in Laboratory Fish: Model Organisms for the Analysis of Gene Function," in Transgenic Animals, Generation and Use (The Netherlands 1997), pp. 387-395.
Young, H. E. et al. "Isolation of Embryonic Chick Myosatellite and Pluripotent Stem Cells" The Journal of Tissue Culture Methods, vol. 14, Issue 2, 1992, pp. 85-92.
Zelickson, B. et al., "Cryolipolysis for Noninvasive Fat Cell Destruction: Initial Results from a Pig Model", 35 Dermatol. Sug., 2009, pp. 1-9.
Zouboulis, C. C. et al., "Current Developments and Uses of Cryosurgery in the Treatment of Keloids and Hypertrophic Scars," Wound Repair and Regeneration, vol. 10, No. 2, 2002, pp. 98-102.

\* cited by examiner

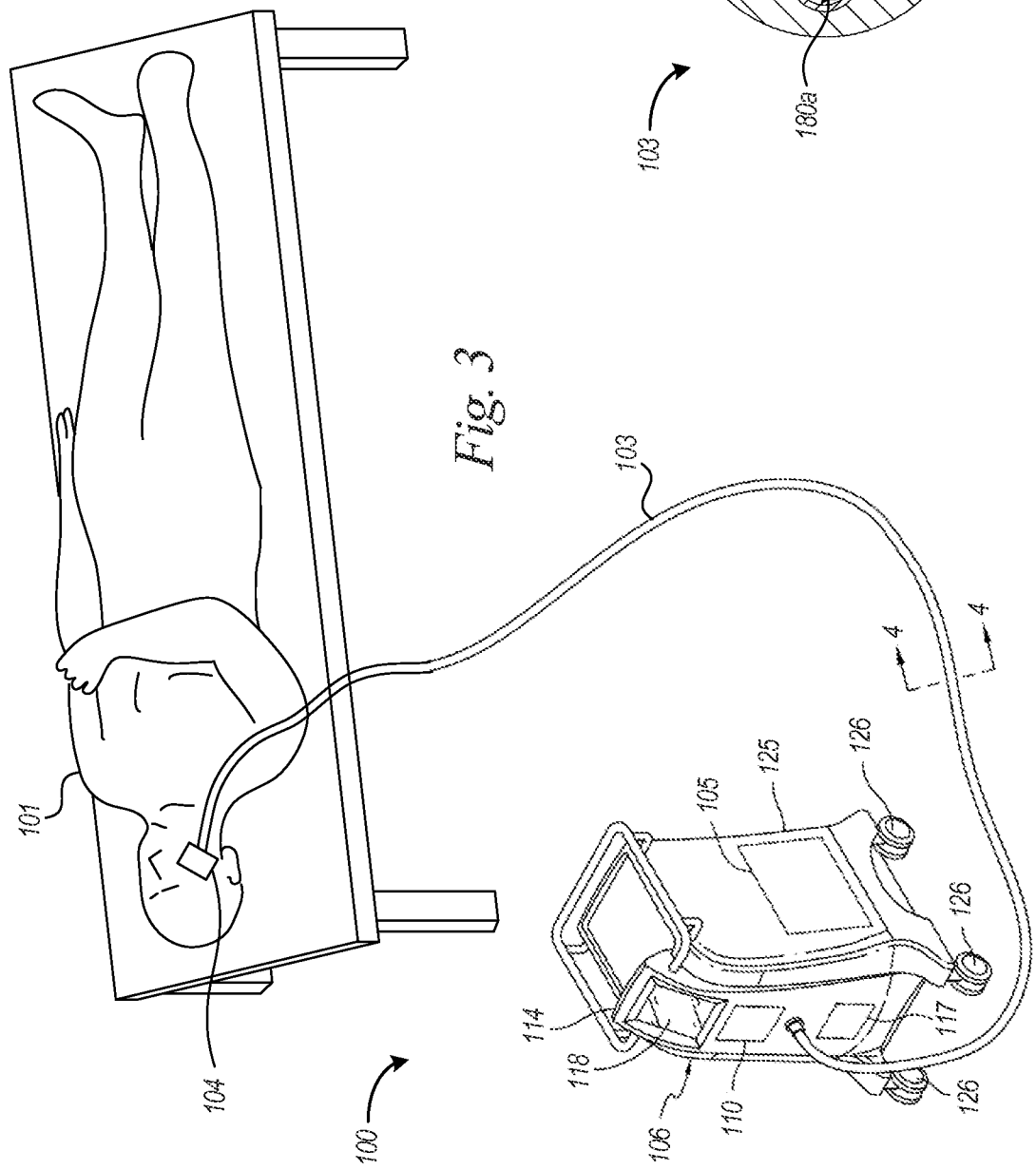
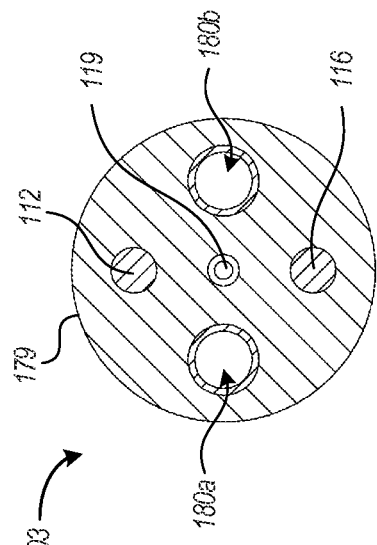

TREATMENT SYSTEMS AND METHODS FOR AFFECTING GLANDS AND OTHER TARGETED STRUCTURES

CROSS-REFERENCE TO RELATED APPLICATIONS

This application is a 35 U.S.C. § 371 U.S. National Phase application of International Application No. PCT/US2015/013971, filed Jan. 30, 2015, which claims priority to U.S. Provisional Patent Application No. 61/934,549, filed Jan. 31, 2014, entitled "COMPOSITIONS, TREATMENT SYSTEMS AND METHODS FOR IMPROVED COOLING OF LIPID-RICH TISSUE;" U.S. Provisional Patent Application No. 61/943,250, filed Feb. 21, 2014, entitled "TREATMENT SYSTEMS, METHODS, AND APPARATUSES FOR IMPROVING THE APPEARANCE OF SKIN;" and U.S. Provisional Patent Application No. 61/943,257, filed Feb. 21, 2014, entitled "TREATMENT SYSTEMS, METHODS AND APPARATUS FOR REDUCING SKIN IRREGULARITIES CAUSED BY CELLULITE," which are incorporated herein by reference in their entireties.

INCORPORATION BY REFERENCE OF COMMONLY-OWNED APPLICATIONS AND PATENTS

The following commonly assigned U.S. Patent Applications and U.S. Patents are incorporated herein by reference in their entirety:

U.S. Patent Publication No. 2008/0287839 entitled "METHOD OF ENHANCED REMOVAL OF HEAT FROM SUBCUTANEOUS LIPID-RICH CELLS AND TREATMENT APPARATUS HAVING AN ACTUATOR";

U.S. Pat. No. 6,032,675 entitled "FREEZING METHOD FOR CONTROLLED REMOVAL OF FATTY TISSUE BY LIPOSUCTION";

U.S. Patent Publication No. 2007/0255362 entitled "CRYOPROTECTANT FOR USE WITH A TREATMENT DEVICE FOR IMPROVED COOLING OF SUBCUTANEOUS LIPID-RICH CELLS";

U.S. Pat. No. 7,854,754 entitled "COOLING DEVICE FOR REMOVING HEAT FROM SUBCUTANEOUS LIPID-RICH CELLS";

U.S. Patent Publication No. 2011/0066216 entitled "COOLING DEVICE FOR REMOVING HEAT FROM SUBCUTANEOUS LIPID-RICH CELLS";

U.S. Patent Publication No. 2008/0077201 entitled "COOLING DEVICES WITH FLEXIBLE SENSORS";

U.S. Patent Publication No. 2008/0077211 entitled "COOLING DEVICE HAVING A PLURALITY OF CONTROLLABLE COOLING ELEMENTS TO PROVIDE A PREDETERMINED COOLING PROFILE";

U.S. Patent Publication No. 2009/0118722, filed Oct. 31, 2007, entitled "METHOD AND APPARATUS FOR COOLING SUBCUTANEOUS LIPID-RICH CELLS OR TISSUE";

U.S. Patent Publication No. 2009/0018624 entitled "LIMITING USE OF DISPOSABLE SYSTEM PATIENT PROTECTION DEVICES";

U.S. Patent Publication No. 2009/0018623 entitled "SYSTEM FOR TREATING LIPID-RICH REGIONS";

U.S. Patent Publication No. 2009/0018625 entitled "MANAGING SYSTEM TEMPERATURE TO REMOVE HEAT FROM LIPID-RICH REGIONS";

U.S. Patent Publication No. 2009/0018627 entitled "SECURE SYSTEM FOR REMOVING HEAT FROM LIPID-RICH REGIONS";

U.S. Patent Publication No. 2009/0018626 entitled "USER INTERFACES FOR A SYSTEM THAT REMOVES HEAT FROM LIPID-RICH REGIONS";

U.S. Pat. No. 6,041,787 entitled "USE OF CRYOPROTECTIVE AGENT COMPOUNDS DURING CRYOSURGERY";

U.S. Pat. No. 8,285,390 entitled "MONITORING THE COOLING OF SUBCUTANEOUS LIPID-RICH CELLS, SUCH AS THE COOLING OF ADIPOSE TISSUE";

U.S. Provisional Patent Application Ser. No. 60/941,567 entitled "METHODS, APPARATUSES AND SYSTEMS FOR COOLING THE SKIN AND SUBCUTANEOUS TISSUE";

U.S. Pat. No. 8,275,442 entitled "TREATMENT PLANNING SYSTEMS AND METHODS FOR BODY CONTOURING APPLICATIONS";

U.S. patent application Ser. No. 12/275,002 entitled "APPARATUS WITH HYDROPHILIC RESERVOIRS FOR COOLING SUBCUTANEOUS LIPID-RICH CELLS";

U.S. patent application Ser. No. 12/275,014 entitled "APPARATUS WITH HYDROPHOBIC FILTERS FOR REMOVING HEAT FROM SUBCUTANEOUS LIPID-RICH CELLS";

U.S. Patent Publication No. 2010/0152824 entitled "SYSTEMS AND METHODS WITH INTERRUPT/RESUME CAPABILITIES FOR COOLING SUBCUTANEOUS LIPID-RICH CELLS";

U.S. Pat. No. 8,192,474 entitled "TISSUE TREATMENT METHODS";

U.S. Patent Publication No. 2010/0280582 entitled "DEVICE, SYSTEM AND METHOD FOR REMOVING HEAT FROM SUBCUTANEOUS LIPID-RICH CELLS";

U.S. Patent Publication No. 2012/0022518 entitled "COMBINED MODALITY TREATMENT SYSTEMS, METHODS AND APPARATUS FOR BODY CONTOURING APPLICATIONS";

U.S. Publication No. 2011/0238050 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS";

U.S. Publication No. 2011/0238051 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS";

U.S. Publication No. 2012/0239123 entitled "DEVICES, APPLICATION SYSTEMS AND METHODS WITH LOCALIZED HEAT FLUX ZONES FOR REMOVING HEAT FROM SUBCUTANEOUS LIPID-RICH CELLS";

U.S. patent application Ser. No. 13/830,413 entitled "MULTI-MODALITY TREATMENT SYSTEMS, METHODS AND APPARATUS FOR ALTERING SUBCUTANEOUS LIPID-RICH TISSUE";

U.S. patent application Ser. No. 13/830,027 entitled "TREATMENT SYSTEMS WITH FLUID MIXING SYSTEMS AND FLUID-COOLED APPLICATORS AND METHODS OF USING THE SAME";

U.S. Provisional Patent Application No. 61/943,251 entitled "TREATMENT SYSTEMS AND METHODS FOR TREATING CELLULITE"; and U.S. Provisional Patent Application No. 61/943,257 entitled "TREATMENT SYSTEMS, METHODS, AND

APPARATUS FOR REDUCING IRREGULARITIES CAUSED BY CELLULITE."

TECHNICAL FIELD

The present disclosure relates generally to treatment systems and methods for affecting target structures in a subject's body. In particular, several embodiments are directed to treatment systems and methods for affecting glands to treat acne, hyperhidrosis, cysts, or other conditions.

BACKGROUND

Exocrine glands found in the skin have a role in maintaining skin health including lubricating, waterproofing, cleansing and/or cooling the skin or hair follicles of the body by excreting water-based, oily and/or waxy substances through skin pores or hair follicles. Overproduction and/or over-secretion of these substances by certain exocrine glands, such as sebaceous glands and sudoriparous glands (e.g., sweat glands), can cause unappealing skin disorders that have proved to be difficult to treat. For example, overproduction of sebum, a waxy substance produced and secreted by sebaceous glands, can lead to formation of comedones (e.g., blackheads, whiteheads, etc.) as well as other inflammatory conditions of the skin associated with acne (e.g., inflamed papules, pustules, nodules, etc.) and can potentially lead to scarring of the skin. Overproducing sebaceous glands associated with hair follicles can be mostly found in highly visible regions of the body, such as on the face, neck, upper chest, shoulders and back, and demand for effective treatments has been and remains quite high.

Hyperhidrosis is a condition associated with excessive sweating and results from the overproduction and secretion of sweat from sweat glands in the skin of mammals. Excessive sweating from eccrine sweat glands, which are distributed almost all over the body, can cause discomfort and embarrassment. For example, focal hyperhidrosis can occur on the palms of the hands, soles of the feet, face and scalp. Apocrine sweat glands, particularly in the axilla (i.e., armpits), have oil-producing cells that can contribute to excessive production and undesirable odor. Treatment for these conditions are often ineffective, non-lasting, and/or have undesirable side-effects.

BRIEF DESCRIPTION OF THE DRAWINGS

In the drawings, identical reference numbers identify similar elements or acts. The sizes and relative positions of elements in the drawings are not necessarily drawn to scale.

FIG. 3 is a partially schematic, isometric view of a treatment system for non-invasively treating targeted structures in a human subjects body in accordance with an embodiment of the technology.

FIG. 4 is a cross-sectional view of a conduit of the treatment system of FIG. 3.

DETAILED DESCRIPTION

A. Overview

Figure 1:
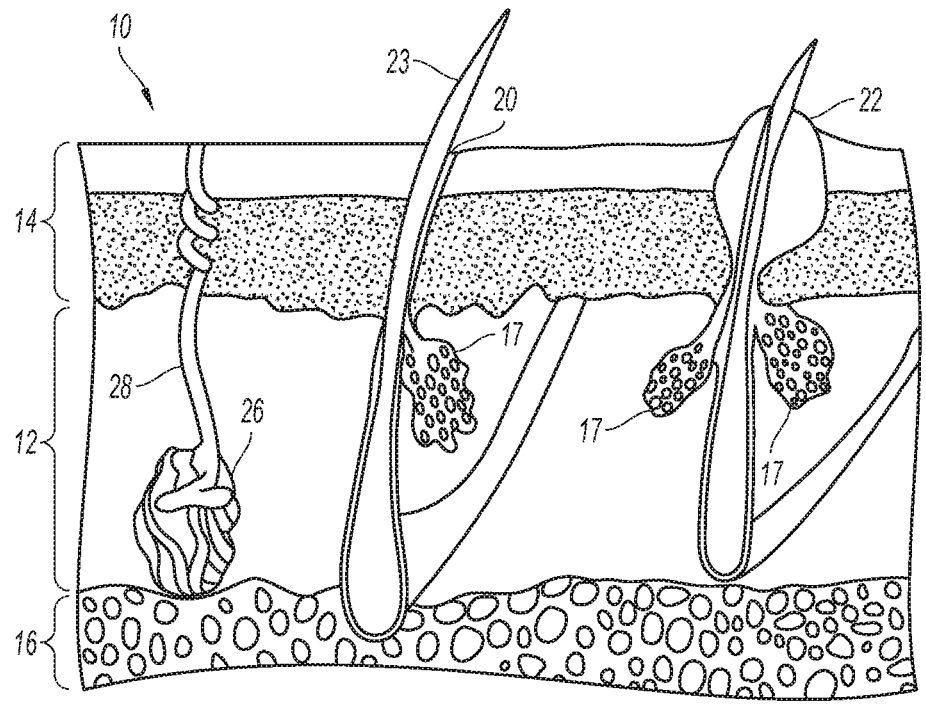
FIG. 1 is a schematic cross-sectional view of the skin, dermis, and subcutaneous tissue of a subject.

The present disclosure describes treatment systems and methods for affecting target structures in tissue. The systems and methods disclosed herein can be used to target glands (e.g., exocrine glands, sebaceous glands, sudoriparous glands, etc.), structures in the skin (e.g., hair follicles, superficial nerves, etc.), and/or layer(s) of tissue (e.g., dermal layer, epidermal layer, layer(s) of the epidermis, etc.). Several of the details set forth below are provided to describe the following examples and methods in a manner sufficient to enable a person skilled in the relevant art to practice, make, and use them. Several of the details and advantages described below, however, may not be necessary to practice certain examples and methods of the technology. Although described examples and methods target glands, the technology can target other structures or features and may include other examples and methods that are within the scope of the technology but are not described in detail. The treatment systems and treatment devices disclosed herein can perform a wide range of cryotherapy procedures.

Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, blocks, stages, or characteristics may be combined in any suitable manner in one or more examples of the technology. The headings provided herein are for convenience only and are not intended to limit or interpret the scope or meaning of the technology.

Various aspects of the technology are directed to treatment systems and methods for affecting target structures in a human subject's body. The target structures can be glands, hair follicles, nerves (e.g., superficial nerves), or one or more layers of tissue (e.g., dermal layer, epidermal layer, layer(s) of the epidermis, etc.). To treat acne, the surface of the subject's skin can be cooled to produce a temperature at or below 0, 5, 10, 15, or 20 degrees C. and to produce either a cooling event or a freeze event in a targeted portion of the skin with sebaceous glands. The skin can be cooled to maintain the cooled state or frozen state of the targeted portion of the skin for a period of time long enough to alter a level of secretion production by the sebaceous glands. The characteristics of the cooling event or freeze event can be controlled to manage thermal injury. Such characteristics include, without limitation, the amount of cooling or freezing, density and distribution of ice crystals, freezing rate, etc. Cryotherapy can affect, without limitation, glandular function, structures of glands (e.g., gland portions, duct portions, etc.), number of glands, and/or sizes of glands.

Freeze events can include partially or completely freezing liquids or lipids proximate to or within glands to destroy, reduce, disrupt, modify, or otherwise affect glands or the supporting anatomical features (e.g., ducts, pores, hair follicles, etc.). In some embodiments, to treat exocrine glands, a subject's skin can be cooled to produce a partial freeze event in a portion of skin with exocrine glands. The level of freezing can be controlled to limit tissue damage, such as tissue damage to non-targeted tissue, damage of targeted tissue (e.g., to avoid excess damage to targeted tissue), and so forth. The subject's skin can be continuously or periodically cooled/heated to adjust the level of freezing. For example, the skin surface can be cooled or heated to increase or decrease, respectively, the number and/or sizes of ice crystals at the target region.

In some embodiments, a method comprises cooling a subject's skin to produce a cooling event in the skin, but not a freeze event. After the cooling event begins, the subject's skin is cooled to maintain the cooling event to alter glands (e.g., gland function, gland size, gland structure, gland number, etc.). The cooling event can alternatively be a freeze event that involves at least partially or totally freezing a target region with the glands so as to alter secretion levels of the glands. In acne treatments, the freeze event can injure sebaceous glands to reduce sebum production. In hyperhidrosis treatments, the freeze event can injure sweat glands to reduce sweating. The location and characteristics of the freeze event can be selected based on treatments to be performed.

Aspects of the technology can include a method for treating a subject's exocrine glands by cooling a surface of a subject's skin with a cooling device to produce a partial or total freeze event in a portion of the skin with exocrine glands. The partial or total freeze event in the patient's skin can be detected. The cooling device and other treatment parameters can be controlled to continue to cool the subject's skin after detecting the partial or total freeze event and to maintain a partially or totally frozen state of the portion of the skin for a period of time long enough to alter a level of production by the exocrine glands. In one embodiment, the period of time is longer than a predetermined threshold period of time, such as 10 seconds, 20 seconds, or other selected period of time. If the epidermis is overly frozen, hyperpigmentation (skin darkening) or hypopigmentation (skin lightening) can result, which is often undesirable. The cooling device and treatment parameters can be controlled so as to not cause either or both hypopigmentation or hyperpigmentation more than a day following treatment.

At least some embodiments are systems and methods for selective non-invasive cooling of tissue sufficiently deep to affect glands. Axilla apocrine sweat glands or eccrine sweat glands on the palms of the hands can be at different tissue depths than sebaceous glands within acne-prone regions (e.g., regions along the face, chest, shoulders, or back). The systems and methods disclosed herein can controllably cool tissue at specific depths for injuring targeted glands. In various embodiments, a zone of maximum cooling or maximum freezing can occur at depths between about 1 mm to about 5 mm, between about 2 mm and about 5 mm, between about 3 mm and about 5 mm, or between about 4 mm and about 5 mm. Other depths can be selected based on the location of the targeted structures. In some embodiments, a treatment site can be cooled to a temperature equal to or lower than about 0° C., −5° C., −10° C., −15° C., −20° C., or −25° C. for a treatment period, and either be in a supercooled state, a partial frozen state, or totally frozen state. The treatment period can be equal to or greater than about 1 second, 2 seconds, 3 seconds, 5 seconds, 30 seconds, 1 minute, 5 minutes, 10 minutes, 30 minutes, or other time periods selected based on the desired thermal injury. In some supercooling embodiments, the skin is cooled to a supercooled temperature and the epidermis is then warmed to a non-freezing temperature. After warming the epidermis, supercooled tissue is nucleated to initiate the freeze event in the supercooled skin. A freezing point of a material is most reliably ascertained by warming frozen material slowly and measuring a temperature at which melting begins to occur. This temperature is generally not ambiguous if the material is slowly warmed. Partial melting will begin to occur at the freezing/melting point. Conversely, if a non-frozen material is cooled, its freezing/melting point is harder to ascertain since it is known that many materials can simply "supercool," that is they can be cooled to a bulk temperature below their freezing/melting point and still remain in a non-frozen state. As used herein, "supercooling," "supercooled," "supercool," etc., refers to a condition in which a material is at a temperature below its freezing/melting point but is still in an unfrozen or mostly unfrozen state.

With or without freezing, at least some embodiments of the technology are directed to controlling a cooling device or providing other means for sufficiently protecting the epidermis from injuries that cause hyperpigmentation (skin darkening) or hypopigmentation (skin lightening). The other means for protection can include, without limitation, heating the epidermis to a non-freezing temperature while deeper tissue remains cold to induce injury thereto and/or applying a cryoprotectant to a surface of the skin to provide freeze protection to the epidermis while allowing deeper tissue or structures to be more affected by the cooling/cold treatment.

Applicators disclosed herein can include one or more elements (e.g., resistive heaters, electrodes, transducers, vibrators, etc.) for delivering energy, such as thermal energy, electromagnetic energy, infrared energy, light energy, ultraviolet energy, radiofrequency energy, microwave energy, ultrasound energy (e.g., low frequency ultrasound, high frequency ultrasound, etc.), mechanical massage, and/or electric fields (e.g., AC or DC electric fields). The energy can inhibit or reduce freeze damage or cooling damage in non-targeted regions. Thermal energy can be used to protect non-targeted tissue, such as facial subcutaneous fat, when cryogenically treating superficial facial dermal structures. Additionally or alternatively, non-targeted regions can be protected by a chemical cryoprotectant. In addition to targeting glands (e.g., exocrine glands such as sebaceous glands, apocrine sweat glands, eccrine sweat glands, etc.), applicators can be configured to target other structures, such as collagen and/or elastin for skin tightening and dermal thickening, nerve tissue (e.g., superficial nerves), and/or hair follicles.

At least some aspects of the technology are directed to systems and methods that enable supercooling of target regions. Aspects of the disclosure are further directed to systems or methods for protecting non-targeted cells, such as cells in the dermal and/or epidermal skin layers, by preventing or limiting thermal damage (e.g., cooling or freeze damage) during dermatological and related aesthetic procedures that require sustained exposure to cold temperatures. For example, treatment systems can supercool treatment sites without causing nucleation and freezing. Non-targeted tissue can be heated to localize the supercooling, and after localizing the supercooled tissue, supercooled body fluids/lipids can be nucleated by various methods to initiate a partial or total freeze and to damage, reduce, disrupt, modify or otherwise affect targeted cells.

In some supercooling embodiments, regions with glands can be supercooled either with or without using any cryoprotectant. Non-targeted region(s) can be heated above their freezing points before initiating crystallization of the supercooled tissue. In certain embodiments for affecting glands in the dermal layer, the skin can be supercooled either with or without affecting the subcutaneous layer. After heating the epidermal layer so that mostly dermal tissue is supercooled, nucleation in the dermal layer can be initiated. Freezing of the supercooled region can be promoted without damaging non-targeted tissue or non-targeted anatomical features. Nucleation can be induced by delivering an alternating current to the tissue, applying a nucleating solution onto the surface of the skin (for example one that includes bacteria which initiate nucleation), applying fields (e.g., electric fields), and/or by creating a mechanical perturbation to the tissue, such as by use of vibration, ultrasound energy, etc.

B. Treatment Sites

FIG. 1 is a schematic cross-sectional view of tissue of a subject in accordance with one embodiment. The subject's skin 10 includes the dermis 12 located between the epidermis 14 and the subcutaneous layer 16. The dermis 12 includes sebaceous glands 17 that produce sebum for moisturizing the skin and hair. Acne is a skin condition typically characterized by excess sebum that may plug hair follicles and/or pores. The level of sebum production may vary between individuals and may vary by body location depending on the number and sizes of the sebaceous glands. Sebum can flow along the healthy hair follicle 20 to moisturize the hair 23 and/or epidermis 14. When the sebaceous glands 17 produce excess sebum, it can collect and/or become trapped in hair follicles. Overproduction and/or entrapment of sebum, the waxy substance produced and secreted by sebaceous glands 17, can lead to formation of comedones (e.g., blackheads, whiteheads, etc.) as well as other inflammatory conditions of the skin associated with acne (e.g., inflamed papules, pustules, nodules, etc.). In some individuals, inflamed follicles and pores can become infected and the condition can potentially lead to scarring of the skin. The illustrated hair follicle 22 is clogged with excess sebum to form a pimple or red spot. Other medical conditions associated with overactive sebaceous glands which produce an excess of sebum include sebaceous cysts, hyperplasia and sebaceous adenoma. Non-medical, but cosmetically unappealing, conditions associated with overactive sebaceous glands include oily skin and/or oily hair (e.g., on the scalp).

Hyperhidrosis is a skin condition characterized by abnormal sweating due to high secretion levels of sweat glands 26. Eccrine sweat glands are controlled by the sympathetic nervous system and regulate body temperature. When an individual's body temperature rises, eccrine sweat glands secrete sweat (i.e., water and other solutes) that flows through a gland tubule 28. The sweat can evaporate from the skin surface to cool the body. Apocrine sweat glands (not shown) secrete an oil-containing sweat into hair follicles 20. The axilla (e.g., armpit) and genital regions often have a higher concentration of apocrine sweat glands. Hyperhidrosis occurs when sweat glands produce and secrete sweat at levels above that required for regulation of body temperature, and the condition can be generalized or localized (i.e., focal hyperhidrosis) to specific body parts (e.g., palms of hands, soles of feet, brow, scalp, face, underarms, etc.).

Figure 2:
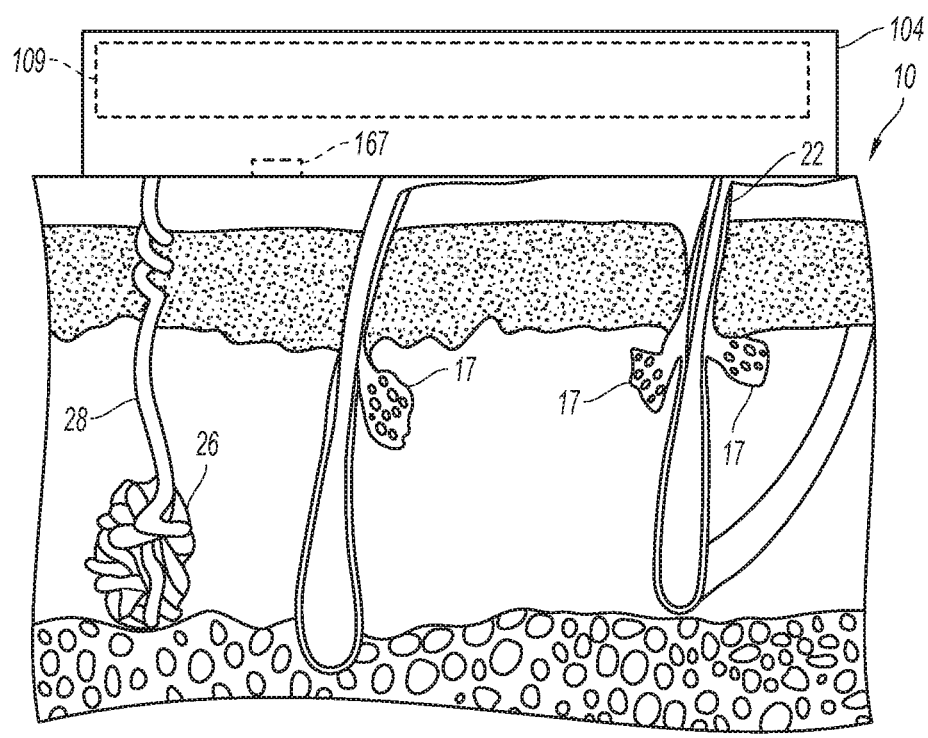
FIG. 2 is a schematic cross-sectional view of the skin, dermis, and subcutaneous tissue of the subject in FIG. 1 after treating sebaceous glands.

FIG. 2 is a schematic cross-sectional view of the skin 10 in FIG. 1 showing a reduction of acne after treatment in accordance with aspects of the present technology. A treatment device in the form of a thermoelectric applicator 104 ("applicator 104") has been applied to and cooled the skin 10 to produce a freeze-induced injury that affected the sebaceous glands 17. Although the reduction in acne is shown while the applicator 104 is applied to the skin 10, it may take a relatively long period of time (e.g., days, weeks, months, etc.) for acne to be reduced after treatment. The sebum production level of the two sebaceous glands 17 along the hair follicle 22 has been substantially reduced to inhibit clogging to minimize, reduce, or eliminate acne. The sweat gland 26 can also be targeted. For example, the applicator 104 can produce a partial or total freeze event or non-freezing cooling event or supercooling event to injure the sweat gland 26 and/or duct 28 in a region of the skin located along the hands, armpits, or other locations with excess sweating. Cryotherapy can be performed any number of times at the same site or different sites to treat acne, hyperhidrosis, or other conditions.

C. Cryotherapy

FIG. 3 and the following discussion provide a general description of an example of a suitable non-invasive treatment system 100 in which aspects of the technology can be implemented. The treatment system 100 can be a temperature-controlled cooling apparatus for cooling tissue at a targeted treatment site to perform cryotherapy. Physiological characteristics affected by cryotherapy can include, without limitation, cellular stability, cell/tissue elasticity, cell size, cell number, and/or gland size or secretion ability (e.g., size/diameter of the duct portion). For example, the treatment system 100 can cool the epidermis, dermis, subcutaneous fat, or other targeted tissue to modify glandular function, reduce gland size, etc. Non-targeted tissue, such as subdermal tissue or tissue adjacent the targeted exocrine glands, can remain generally unaffected. In various embodiments, the treatment system 100 can be configured to cool the skin of the patient to selectively affect (e.g., injure, damage, kill) secreting exocrine glandular cells. In a particular example, cooling can produce a cold shock response to modify a secretion volume from a targeted exocrine gland of the epidermis and/or dermis by affecting protein proliferation and other cellular functions. Those skilled in the relevant art will appreciate that other examples of the disclosure can be practiced with other treatment systems and treatment protocols, including invasive, minimally invasive, other non-invasive medical treatments.

In one example, lipid-producing cells residing in or at least proximate to sebaceous glands (e.g., glandular epithelial cells) present in the dermis of a target region can be targeted by the treatment system 100 for the treatment of acne or other skin condition. The lipid-producing cells residing in or proximate to sebaceous glands contribute to production of sebum, the waxy and oily secretion that can contribute to acne. For example, the treatment system 100 can be configured to reduce a temperature of a dermal layer of skin to reduce the temperature of lipid-producing cells residing in or at least proximate to sebaceous glands such that the targeted lipid-producing cells excrete a lower amount of sebum, such that there are fewer lipid-producing cells resulting in less sebum production within the targeted sebaceous glands, or in another embodiment, such that the sebaceous glands are destroyed. The treatment system 100 can be configured, for example, to reduce a subject's acne by cooling acne-prone regions of the body.

In another example, secreting glandular cells residing in axilla apocrine sweat glands can be targeted by the treatment system 100 for the treatment of hyperhidrosis. Apocrine sweat glands comprise a coiled secretory portion located at the junction of the dermis and the subcutaneous fat, and a duct portion that funnels the secreted sweat substance into a portion of a hair follicle. Secreting glandular cells residing in the coiled secretory portion between the dermis and the subcutaneous layers produce an oily compound and create a secretion substance that also includes water and other solutes, such as minerals, lactate and urea to form apocrine sweat. The treatment system 100 can be configured to reduce a temperature of a dermal layer of skin (e.g., at or near the axilla) to reduce the temperature of secreting glandular cells residing in the coiled portion of the apocrine sweat glands such that the targeted cells excrete a lower amount of oil-containing sweat, such that there are fewer sweat-producing cells resulting in less sweat/oil production within the targeted apocrine sweat glands, or in another embodiment, such that the apocrine sweat glands are destroyed. In yet another embodiment, secreting glandular cells residing in or proximate to eccrine sweat glands (e.g., in the palms of the hands, soles of the feet, scalp, face, axilla region, etc.) can be targeted by the treatment system 100 for the treatment of focal hyperhidrosis at those treatment sites.

Referring to FIG. 3, the applicator 104 is suitable for altering a function of a gland residing in skin without affecting subcutaneous tissue (e.g., subcutaneous adipose tissue, etc.). The applicator 104 can be suitable for modifying a secretion volume, level, biochemical content, or other factor from targeted exocrine glands (e.g., sebaceous glands 17 or sweat glands 26 shown in FIG. 1) by cooling the skin without permanently altering cells of non-targeted tissue (e.g., deep dermal tissue, subdermal tissue, etc.). Without being bound by theory, the effect of cooling selected cells (e.g., glandular secreting cells, hair follicles, etc.) is believed to result in, for example, protein alteration (e.g., synthesis of heat shock proteins, stress proteins, etc.), cell size alteration, cell division, wound remodeling (e.g., thickening of the epidermis, contraction of the epidermis, etc.), fibrosis, and so forth. By cooling the skin to a sufficient low temperature, target cells that contribute to the presence of undesired features can be selectively affected while non-targeted tissue can be unaffected.

The applicator 104 can be used to perform a wide range of different cryotherapy procedures. One cryotherapy procedure involves at least partially freezing tissue (e.g., cellular structures, intracellular fluid, extracellular fluid, connective tissue etc.) in a target tissue region to form crystals that alter targeted cells to modify a glandular secretion characteristic (e.g., volume, content, etc.) without destroying a significant amount of cells in the skin. To avoid destroying skin cells in a partial freeze embodiment and in an embodiment where tissue is not partially frozen, the surface of the patient's skin can be cooled to temperatures no lower than, for example, −40° C. for a duration short enough to avoid, for example, excessive ice formation, permanent thermal damage, or lightening or darkening skin, such as significant hypopigmentation (including long-lasting or permanent hypopigmentation) or hyperpigmentation (including long-lasting or permanent hyperpigmentation) in a period of time following a treatment, such as several hours; one, two, three days; or one, two, three weeks; and longer periods of time following a treatment. In another embodiment, undue destruction of skin cells, epidermal cells in particular, can be avoided by applying heat to the surface of the patient's skin to heat these skin cells above their freezing temperature. The patient's skin can be warmed to at least about −30° C., −25° C., −20° C., −15° C., −10° C., 0° C., 10° C., 20° C., 30° C., or other temperature sufficient to avoid, for example, excessive ice formation, permanent thermal damage, or significant hypopigmentation or hyperpigmentation of the non-targeted and/or epidermal tissue. In some treatments, skin can be cooled to produce partial or total freeze events that cause apoptotic damage to skin tissue without causing significant damage to adjacent subcutaneous tissue. Apoptosis, also referred to as "programmed cell death", of the skin tissue can be a genetically-induced death mechanism by which cells slowly self-destruct without incurring damage to surrounding tissues. Other cryotherapy procedures may cause non-apoptotic responses.

In some tissue-freezing procedures, the applicator 104 can controllably freeze tissue (e.g., organic matter, inorganic matter, etc.) within a tissue region and can detect the freeze event. After detecting the freeze event, the applicator 104 can periodically or continuously remove heat from the target tissue to keep a volume of target tissue frozen for a suitable predetermined length of time to elicit a desired response and yet a short enough period of time to not cause any unwanted or undesired side effects, such as hypopigmentation and/or hyperpigmentation. The detected freeze event can be a partial freeze event, a complete freeze event, etc. In some embodiments, the controlled freezing causes tightening of the skin, thickening of the skin, and/or a cold shock response at the cellular level in the skin. In one tissue-freezing treatment, the applicator 104 can produce a partial or total freeze event that includes, without limitation, partial or full thickness freezing of the patient's skin for a relatively short limit to avoid cooling the adjacent subcutaneous tissue to a low enough temperature for subcutaneous cell death. The freezing process can include forming ice crystals in intracellular and/or extracellular fluids, and the ice crystals can be small enough to avoid disrupting membranes so as to prevent significant permanent tissue damage, such as necrosis. Some partial freeze events can include freezing mostly extracellular material without freezing a substantial amount of intercellular material. In other procedures, partial freeze events can include freezing mostly intercellular material without freezing a substantial amount of extracellular material. The frozen target tissue can remain in the frozen state long enough to affect the target tissue but short enough to avoid damaging non-targeted tissue or damaging an undue amount of the target tissue. For example, the duration of the freeze event can be shorter than about 20 seconds, 30 seconds, or 45 seconds or about 1, 2, 3, 4, 5 or 10 minutes. The frozen tissue can be thawed to prevent necrosis and, in some embodiments, can be thawed within about 20 seconds, 30 seconds, or 45 seconds or about 1, 2, 3, 4, 5, or 10 minutes after initiation of the freeze event.

The mechanisms of cold-induced tissue injury in cryotherapy can also involve direct cellular injury (e.g., damage to the cellular machinery) and/or vascular injury in embodiments where freezing occurs and in embodiments where freezing does not occur. For example, cell injury can be controlled by adjusting thermal parameters, including (1) cooling rate, (2) end (or minimum) temperature, (3) time held at the minimum temperature (or hold time), (4) temperature profile, and (5) thawing rate. In one example, increasing the hold time can allow the intracellular compartments to equilibrate with the extracellular space, thereby increasing cellular dehydration. Another mechanism of cold-induced injury is cold and/or freeze-stimulated immunologic injury. Without being bound by theory, it is believed that after cryotherapy, the immune system of the host is sensitized to the disrupted tissue (e.g., lethally damaged tissue, undamaged tissue, or sublethally injured tissue), which can be subsequently destroyed by the immune system.

One mechanism to selectively affect oil and/or sebum-producing and secreting glandular cells is to cool the targeted tissue to temperatures that affect lipid-rich cells (which generally freeze or are damaged at temperatures which are higher than temperatures at which non-lipid rich cells are damaged) but that do not negatively affect non-lipid rich cells, such as other cells in the epidermal and dermal layers at or proximate to the treatment site which have lower temperature damage thresholds. The treatment system 100 can be configured to cool the subject's skin for a period of time long enough so that lipid-rich cells (sebum or oil-producing cells residing in or at least proximate to exocrine glands) in the dermal layer are substantially affected to cause, for example, apoptosis. Apoptosis of lipid-rich cells may be a desirable outcome for beneficially altering (e.g., reducing) glandular function that may contribute to an undesirable appearance (e.g., acne, hyperhidrosis, etc.). Apoptosis of glandular lipid-rich cells can involve ordered series of biochemical events that induce cells to morphologically change. These changes include cellular blebbing, loss of cell membrane asymmetry and attachment, cell shrinkage, chromatin condensation, and chromosomal DNA fragmentation. Injury via an external stimulus, such as cold exposure, is one mechanism that can induce apoptosis in cells. Nagle, W. A., Soloff, B. L., Moss, A. J. Jr., Henle, K. J. "Cultured Chinese Hamster Cells Undergo Apoptosis After Exposure to Cold but Nonfreezing Temperatures" *Cryobiology* 27, 439-451 (1990). One aspect of apoptosis, in contrast to cellular necrosis (a traumatic form of cell death causing, and sometimes induced by, local inflammation), is that apoptotic cells express and display phagocytic markers on the surface of the cell membrane, thus marking the cells for phagocytosis by, for example, macrophages. As a result, phagocytes can engulf and remove the dying cells (e.g., the lipid-rich cells) without eliciting an immune response.

Without being bound by theory, one mechanism of apoptotic lipid-rich cell death by cooling is believed to involve localized crystallization of lipids within the adipocytes at temperatures that may or may not induce crystallization in non-lipid-rich cells. The crystallized lipids may selectively injure these cells, inducing apoptosis (and may also induce necrotic death if the crystallized lipids damage or rupture the bilayer lipid membrane of the glandular cell). Another mechanism of injury involves the lipid phase transition of those lipids within the cell's bilayer lipid membrane, which results in membrane disruption, thereby inducing apoptosis. This mechanism is well documented for many cell types and may be active when lipid-rich cells, are cooled. Mazur, P., "Cryobiology: the Freezing of Biological Systems" Science, 68: 939-949 (1970); Quinn, P. J., "A Lipid Phase Separation Model of Low Temperature Damage to Biological Membranes" Cryobiology, 22: 128-147 (1985); Rubinsky, B., "Principles of Low Temperature Preservation" *Heart Failure Reviews,* 8, 277-284 (2003). Other possible mechanisms of lipid-rich cell damage, described in U.S. Pat. No. 8,192,474, relates to ischemia/reperfusion injury that may occur under certain conditions when such cells are cooled as described herein. For instance, during treatment by cooling as described herein, targeted glandular tissue may experience a restriction in blood supply and thus be starved of oxygen due to isolation while pulled into, e.g., a vacuum cup, or simply as a result of the cooling which may affect vasoconstriction in the cooled tissue. In addition to the ischemic damage caused by oxygen starvation and the build-up of metabolic waste products in the tissue during the period of restricted blood flow, restoration of blood flow after cooling treatment may additionally produce reperfusion injury to the glandular cells due to inflammation and oxidative damage that is known to occur when oxygenated blood is restored to tissue that has undergone a period of ischemia. This type of injury may be accelerated by exposing the glandular cells to an energy source (via, e.g., thermal, electrical, chemical, mechanical, acoustic or other means) or otherwise increasing the blood flow rate in connection with or after cooling treatment as described herein. Increasing vasoconstriction in such glandular tissue by, e.g., various mechanical means (e.g., application of pressure or massage), chemical means or certain cooling conditions, as well as the local introduction of oxygen radical-forming compounds to stimulate inflammation and/or leukocyte activity in glandular tissue may also contribute to accelerating injury to such cells. Other yet-to-be understood mechanisms of injury may also exist.

In addition to the apoptotic mechanisms involved in lipid-rich cell death, local cold exposure may induce lipolysis (i.e., fat metabolism) of lipid-rich cells. For example, cold stress has been shown to enhance rates of lipolysis from that observed under normal conditions which serves to further increase the volumetric reduction of lipid-rich cells. Vallerand, A. L., Zamecnik. J., Jones, P. J. H., Jacobs, I. "Cold Stress Increases Lipolysis, FFA Ra and TG/FFA Cycling in Humans" *Aviation, Space and Environmental Medicine* 70, 42-50 (1999).

Without being bound by theory, the effect of cooling on lipid-rich cells is believed to result in, for example, membrane disruption, shrinkage, disabling, destroying, removing, killing, or another method of lipid-rich cell alteration. For example, when cooling glandular tissue in the dermal layer to a temperature lower than 37° C., lipid-rich cells (e.g., sebum-producing cells within sebaceous glands, oil-producing cells within sweat glands) can selectively be affected. In general, the remaining cells in the epidermis and dermis of the subject 101 have lower amounts of lipids compared to the secreting lipid-rich cells forming portions of the glandular tissue. Since lipid-rich cells are more sensitive to cold-induced damage than non-lipid-rich cells, it is possible to use non-invasive or minimally invasive cooling to destroy lipid-rich cells without destroying the overlying or surrounding skin cells. In some embodiments, lipid-rich cells within secretory glands are destroyed while the appearance of overlying skin is improved.

Lipid-containing cells are more easily damaged by low temperatures than the non-lipid rich dermal and epidermal cells, and as such, the treatment system 100 can be used to cool the desired layers of skin at the treatment sites to a temperature above the freezing point of water, but below the freezing point of fat. It is believed that the temperatures can be controlled to manage damage in the non-lipid-rich cells of the epidermis and/or dermis via, for example, intracellular and/or extracellular ice formation. Excessive ice formation may rupture the cell wall and may also form sharp crystals that locally pierce the cell wall as well as vital internal organelles. Ice crystal initiation and growth can be managed to avoid cell death in the non-targeted portions of the skin. When extracellular water freezes to form ice, the remaining extracellular fluid becomes progressively more concentrated with solutes. The high solute concentration of the extracellular fluid may cause intracellular fluid to be driven through the semi-permeable cellular wall by osmosis resulting in cell dehydration. The applicator 104 can reduce the temperature of the lipid-rich cells found in the targeted glandular tissue such that the lipid rich cells are destroyed while the temperature of the remaining skin cells are maintained at a high enough temperature to produce non-destructive freeze events in the skin. Cryoprotectants and/or thermal cycling can prevent destructive freeze events in the non-targeted skin tissue.

At least some aspects of the technology are directed to systems and methods of treating a patient by cooling a surface of the patient's skin to a temperature sufficiently low to cause supercooling of targeted tissue below the skin surface. The surface of the skin can then be heated to a non-supercooled temperature while the targeted tissue remains in a supercooled state. After heating the non-targeted tissue, the supercooled targeted tissue can be controllably frozen. In some embodiments, nucleation can be controlled to cause partial or total freezing. The applicator 104 can be kept generally stationary relative to the treatment site during cooling to avoid pressure changes that would cause nucleation. After heating non-targeted tissue, the applicator can cause nucleation in the supercooled targeted tissue by, for example, varying applied pressures, delivering energy (e.g., ultrasound energy, RF energy, ultrasound energy), applying fields (e.g., electric fields), or providing other perturbations (e.g., vibrations, pulses, etc.), as well as combinations thereof. Because the non-targeted tissue has been warmed to a non-supercooled state, it does not experience a freeze event. In some embodiments, the applicator can include one or more movable plates (e.g., plates movable to vary applied pressures), rotatable eccentric masses, ultrasound transducers, electrical current generators, or other elements capable of providing nucleating perturbations. Vacuum applicators can increase and decrease vacuum levels to massage tissue, vary applied pressures, etc.

Once catalyzed, the partial or total freeze event can be detected, and a cooling device associated with the treatment system 100 can be controlled to continue cooling the patient's skin so as to maintain a frozen state of targeted tissue for a desired period of time. The skin can be periodically or continuously cooled to keep a sufficient volume of the tissue in a frozen state. In some embodiments, the targeted tissue can be kept frozen for longer or shorter than about, for example, 1 second, 5 seconds, 10 seconds, 20 seconds, 30 seconds, 1 minute, several minutes, or other time period selected to reduce or limit frostbite or necrosis. Further, the temperature of the upper tissue of the skin can be detected, and the treatment system can be controlled to apply heat to the surface of the patient's skin for a preselected period of time to prevent freezing of non-targeted tissue. The preselected period of time can be longer or shorter than about 1, 2, 3, 4, or 5 seconds. Accordingly, non-targeted tissue can be protected without using a chemical cryoprotectant that may cause unwanted side effects. Alternatively, a cryoprotectant can also be used if an additional margin of safety for some tissue, such as the epidermis, is desired.

D. Treatment Systems and Methods of Treatment

FIG. 3 is a partially schematic, isometric view of a treatment system for non-invasively treating targeted structures in a human subjects body in accordance with an embodiment of the technology. The treatment system 100 can include the applicator 104, a connector 103, and a base unit 106. After applying the applicator 104 to a subject 101, it can cool cells in or associated with targeted glands. For example, the applicator 104 can be applied to acne-prone regions and can transcutaneously cool skin to reduce the temperature of lipid-producing cells residing in or at least proximate to sebaceous glands (e.g., glandular epithelial cells) to lower the amount of secreted sebum and thereby eliminate, reduce, or limit acne. The applicator 104 can also cool sweat glands and associated structures to treat hyperhidrosis.

The connector 103 can be an umbilical cord that provides energy, fluid, and/or suction from the base unit 106 to the applicator 104. The base unit 106 can include a fluid chamber or reservoir 105 (illustrated in phantom line) and a controller 114 carried by a housing 125 with wheels 126. The base unit 106 can include a refrigeration unit, a cooling tower, a thermoelectric chiller, heaters, or any other devices capable of controlling the temperature of coolant in the fluid chamber 105 and can be connectable to an external power source and/or include an internal power supply 110 (shown in phantom line). The power supply 110 can provide electrical energy (e.g., a direct current voltage) for powering electrical elements of the applicator 104. A municipal water supply (e.g., tap water) can be used in place of or in conjunction with the fluid chamber 105. In some embodiments, the system 100 includes a pressurization device 117 that can provide suction and can include one or more pumps, valves, and/or regulators. Air pressure can be controlled by a regulator located between the pressurization device 117 and the applicator 104. If the vacuum level is too low, tissue may not be adequately (or at all) held against the applicator 104, and the applicator 104 may tend to move along the patient's skin. If the vacuum level is too high, undesirable patient discomfort and/or tissue damage could occur. A vacuum level can be selected based on the characteristics of the tissue and desired level of comfort.

An operator can control operation of the treatment system 100 using an input/output device 118 of the controller 114. The input/output device 118 can display the state of operation of the applicator 104 and treatment information. In some embodiments, the controller 114 can exchange data with the applicator 104 via a wired connection or a wireless or an optical communication link and can monitor and adjust treatment based on, without limitation, one or more treatment profiles and/or patient-specific treatment plans, such as those described, for example, in commonly assigned U.S. Pat. No. 8,275,442. In some embodiments, the controller 114 can be incorporated into the applicator 104 or another component of the system 100.

Upon receiving input to start a treatment protocol, the controller 114 can cycle through each segment of a prescribed treatment plan. Segments may be designed to freeze tissue, thaw tissue, supercool tissue, nucleate supercooled tissue, and so on. In so doing, the power supply 110 and the fluid chamber 105 can provide power and coolant to one or more functional components of the applicator 104, such as thermoelectric coolers (e.g., TEC "zones"), to begin a cooling cycle and, in some embodiments, activate features or modes such as vibration, massage, vacuum, etc. The controller 114 can receive temperature readings from temperature sensors, which can be part of the applicator 104 or proximate to the applicator 104, the patient's skin, a patient protection device, etc. It will be appreciated that while a target region of the body has been cooled or heated to the target temperature, in actuality that region of the body may be close but not equal to the target temperature, e.g., because of the body's natural heating and cooling variations. Thus, although the system 100 may attempt to heat or cool tissue to the target temperature or to provide a target heat flux, a sensor may measure a sufficiently close temperature or heat flux. If the target temperature or the flux has not been reached, power can be increased or decreased to change heat flux to maintain the target temperature or "set-point" selectively to affect targeted tissue.

FIG. 4 is a cross-sectional view of the connector 103 taken along line 4-4 of FIG. 3 in accordance with at least some embodiments of the technology. The connector 103 can be a multi-line or multi-lumen conduit with a main body 179 (e.g., a solid or hollow main body), a supply fluid line or lumen 180a ("supply fluid line 180a"), and a return fluid line or lumen 180b ("return fluid line 180b"). The main body 179 may be configured (via one or more adjustable joints) to "set" in place for the treatment of the subject. The supply and return fluid lines 180a, 180b can be tubes made of polyethylene, polyvinyl chloride, polyurethane, and/or other materials that can accommodate circulating coolant, such as water, glycol, synthetic heat transfer fluid, oil, a refrigerant, and/or any other suitable heat conducting fluid. In one embodiment, each fluid line 180a, 180b can be a flexible hose surrounded by the main body 179. Referring to FIGS. 3 and 4, coolant can be continuously or intermittently delivered to the applicator 104 via the supply fluid line 180a and can circulate through the applicator 104 to absorb heat. The coolant, which has absorbed heat, can flow from the applicator 104 back to the base unit 106 via the return fluid line 180b. For warming periods, the base unit 106 (FIG. 3) can heat the coolant such that warm coolant is circulated through the applicator 104. Referring now to FIG. 4, the connector 103 can also include one or more electrical lines 112 for providing power to the applicator 104 (FIG. 3) and one or more control lines 116 for providing communication between the base unit 106 (FIG. 3) and the applicator 104 (FIG. 3). To provide suction, the connector 103 can include one or more vacuum tubes or lines 119.

Figure 5:
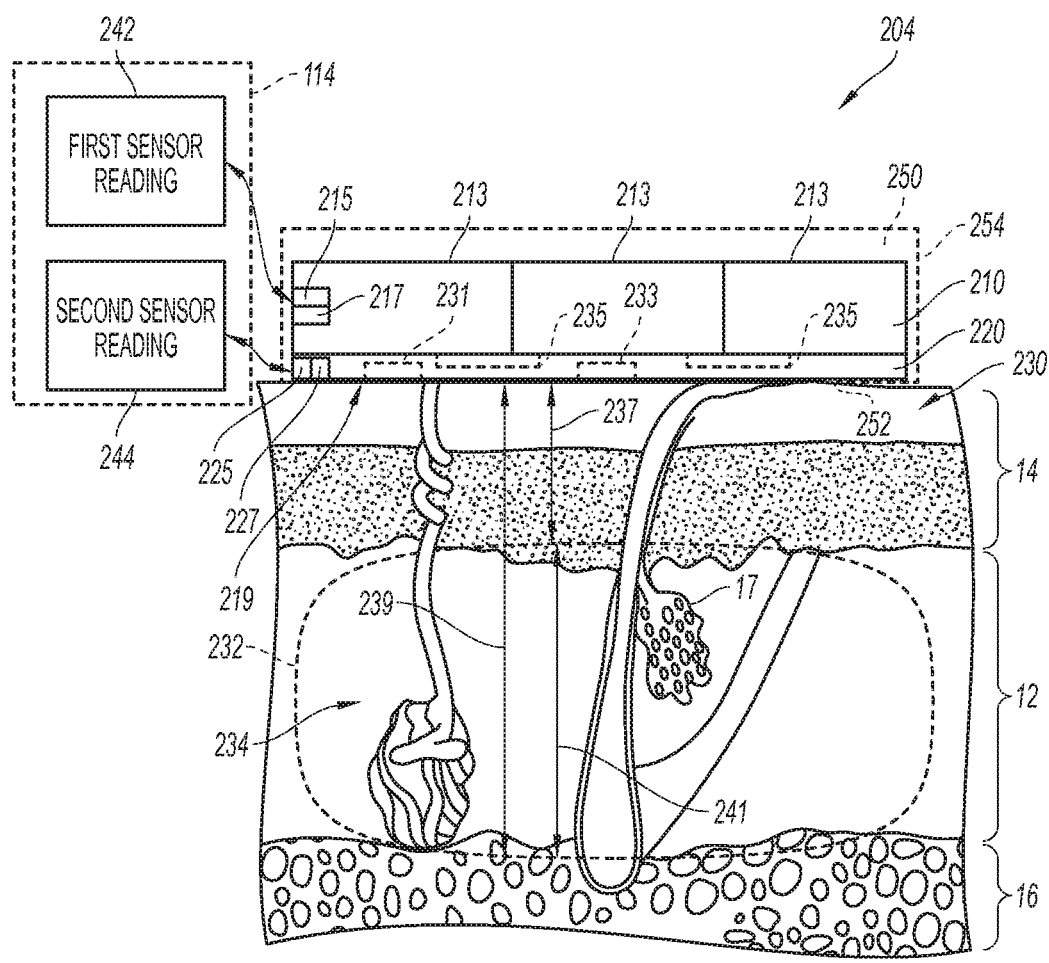
FIG. 5 is a cross-sectional view of a treatment device applied to a treatment site in accordance with an embodiment of the technology.

FIG. 5 is a schematic cross-sectional view of a treatment device in the form a non-invasive applicator 204 suitable for the treatment system 100 in accordance with an embodiment of the present technology. The applicator 204 can cool tissue to produce a thermal event (e.g., supercooling event, freezing event, cooling event, etc.) in a targeted cooling or event zone 232 (shown in phantom line). The controller 114 can be programmed to cause the applicator 204 to cool the subject's skin after detecting the thermal event (e.g., freeze event, supercooling event, reaching a target temperature with or without causing a freeze event, or other detectable thermal event) so that the thermal event lasts a sufficient period of time to substantially alter secretion production levels of the glands. In some procedures, a cooling event can last long enough to permanently decrease production levels of the glands in the event zone 232 in which most significant damage occurs. For example, most or substantially all the sebaceous glands 17 in the event zone 232 can be destroyed, reduced, or otherwise altered to reduce or otherwise modify sebum production.

A central region 234 of the event zone 232 can be deeper than most of the epidermal layer 14 to avoid or limit damage to epidermal tissue which could lead to undesired skin coloration changes. A distance 237 between the surface of the skin and the event zone 232 can be generally equal to or greater than the thickness of the epidermis 14 and, in some embodiments, can be between about 0.1 mm to about 1.5 mm, between about 0.5 mm to about 1.5 mm, or other distances selected to keep thermal damage to epidermal tissue at or below an acceptable level. The event zone 232 can be at a maximum depth 239 between about 0.25 mm to about 5 mm, between about 0.25 mm to about 6 mm, between about 0.3 mm to about 5 mm, between about 0.3 mm to about 6 mm, between about 0.5 mm to about 5 mm, between about 0.5 mm to about 6 mm, or other depths selected to avoid or limit injures to deeper non-targeted tissue (e.g., subcutaneous tissue 16) or structures. The height 241 of the event zone 232 can be between about between about 0.1 mm to about 6 mm, between about 0.1 mm to about 3.5 mm, between about 0.3 mm to about 5 mm, between about 1 mm to about 3 mm, or other heights selected based on the thickness of the dermis 12. For example, the height 241 can be slightly greater than the thickness of the dermis 12 to keep thermal-injuries, if any, to the epidermis 14 and/or subcutaneous layer 16 at an acceptable level. In some embodiments, the event zone 232 can be generally centered in the dermis 12, and the height 241 can be less than the thickness of the dermis 12. Adjacent epidermal and subdermal tissue may also be cooled but can be at a sufficiently high temperature to avoid or limit thermal injury. The location and dimensions (e.g., height 241, width, length, etc.) of the event zone 232 can be selected based on the location of the targeted structures, tissue characteristics at the target site, etc. In some embodiments, the event zone 232 can comprise significant amounts of epidermal and dermal tissue. For example, the event zone 232 can comprise most of the tissue located directly between the cooled heat-exchanging surface 219 and the subcutaneous tissue 16. In some procedures, at least about 60%, 70%, 80%, 90%, or 95% of the tissue directly between the heat-exchanging surface 219 and the subcutaneous layer 16 can be located within the event zone 232. Heating, cryoprotectants, and/or supercooling techniques can be used to avoid injury to the epidermal tissue.

The applicator 204 can include a cooling device 210 and an interface layer 220. The cooling device 210 can include, without limitation, one or more thermoelectric coolers 213, each including one or more the thermoelectric elements (e.g., Peltier-type TEC elements) powered by electrical energy from a treatment tower or base unit (e.g., base unit 106 of FIG. 3) or another power source. The thermoelectric coolers 213 can also include controllers, temperature regulators, sensors, and other electrical components. For example, each thermoelectric cooler 213 can include an array of individually controlled thermoelectric elements and a controller. In some embodiments, the controller 114 can be programmed to control operation of the thermoelectric coolers 213 to remove heat from tissue at a sufficient rate to produce a cooling event (e.g., a freeze or non-freeze event) that can cause destruction of targeted cells. In freeze event embodiments, ice crystals may nucleate and grow in the event zone 232 and can damage cells to inhibit or otherwise affect gland function, but they may also locally pierce a sufficient amount of the cell walls to destroy the glands.

The applicator 204 can include sensors configured to measure tissue impedance, pressure applied to the subject, optical characteristics of tissue, and/or tissue temperatures. As described herein, sensors can be used to monitor tissue and, in some embodiments, to detect events. The number and types of sensors can be selected based on the treatment to be performed. In some embodiments, the applicator 204 can include a communication component 215 that communicates with the controller 114 to provide a first sensor reading 242, and a sensor 217 that measures, e.g., temperature of the cooling device 210, heat flux across a surface of or plane within the cooling device 210, tissue impedance, application force, tissue characteristics (e.g., optical characteristics), etc. The interface layer 220 can be a plate, a film, a covering, a sleeve, a substance reservoir or other suitable element described herein and, in some embodiments, may serve as the patient protection device described herein.

The interface layer 220 can also contain a similar communication component 225 that communicates with the controller 114 to provide a second sensor reading 244 and a sensor 227 that measures, e.g., the skin temperature, temperature of the interface layer 220, heat flux across a surface of or plane within the interface layer 220, contact pressure with the skin of the patient, etc. For example, one or both of the communication components 215, 225 can receive and transmit information, such as temperature and/or heat flux information as determined by one or both of sensors 217, 227. The sensors 217, 227 are configured to measure a parameter of the interface without substantially impeding heat transfer between the applicator 204 and the patient's skin.

In certain embodiments, the applicator 204 can include a sleeve or liner 250 (shown schematically in phantom line) for contacting the patient's skin 230, for example, to prevent direct contact between the applicator 204 and the patient's skin 230, and thereby reduce the likelihood of cross-contamination between patients, minimize cleaning requirements for the applicator 204, etc. The sleeve 250 can include a first sleeve portion 252 and a second sleeve portion 254 extending from the first sleeve portion. The first sleeve portion 252 can contact and/or facilitate contact of the applicator 204 with the patient's skin 230, while the second sleeve portion 254 can be an isolation layer extending from the first sleeve portion 252. The second sleeve portion 254 can be constructed from latex, rubber, nylon, Kevlar®, or other substantially impermeable or semi-permeable material. The second sleeve portion 254 can prevent contact between the patient's skin 230 and the applicator 204, among other things. Further details regarding a patient protection device may be found in U.S. Patent Publication No. 2008/0077201.

The applicator 204 can be manually held against the subject's skin and can also include a belt or other retention devices (not shown) for holding the applicator 204 against the skin. The belt may be rotatably connected to the applicator 204 by a plurality of coupling elements that can be, for example, pins, ball joints, bearings, or other types of rotatable joints. Alternatively, retention devices can be rigidly affixed to the end portions of the interface layer 220. Further details regarding suitable belt devices or retention devices may be found in U.S. Patent Publication No. 2008/0077211. In conjunction with or in place of a retention device, a vacuum can assist in forming a contact between the applicator 204 (such as via the interface layer 220 or sleeve 250) and the patient's skin 230.

The sensors 217, 227 can serve as event detect sensors that provide output (e.g., sensor readings 242, 244) collected in real-time because real-time processing of such output can help correctly and efficaciously administer treatment. The output can be detected temperatures, heat fluxes, optical characteristics of tissue, mechanical characteristics of tissue, etc. In one example, real-time data processing is used to detect cooling events and to determine a period of time to continue cooling the patient's skin after one or more cooling events are detected. Tissue can be monitored to keep a desired region or volume of tissue in the cooled state (e.g., at least partially or totally frozen state) for a period of time selected by the controller 114 or an operator. The period of time can be equal to or longer than about, for example, 5 seconds, 10 seconds, 30 seconds, 1, 2, 3, 4, 5, 6, 7, 8, 9, 10, 30 minutes, 1 hour, or other suitable period of time. In some procedures, the cooling event is a freeze event that lasts a period of time which is longer than 10 seconds and shorter than 10 minutes.

Optionally, the applicator 204 can include one or more features used with supercooling. For example, the interface layer 220 can include one or more nucleation elements 231, 233 in the form of positive and negative electrodes for heating the skin using alternating current heating. For radiofrequency induced nucleation, the nucleation elements 231, 233 can be radiofrequency electrodes. The power supply 110 (FIG. 3) can include an RF generator for driving the elements 231, 233. The nucleation elements 231, 233 can also be configured to provide changes in applied pressure to cause nucleation. Any number of different types of nucleation elements can be incorporated into the interface layer 220 or other components of the applicator 204 to provide the ability to controllably nucleate supercooled tissue.

Although the thermoelectric elements 213 can heat tissue, the applicator 204 can also include dedicated heating elements used to, for example, thaw tissue. FIG. 5 shows the interface layer 220 including heaters 235 for generating heat delivered to the surface of the skin 230. The heaters 235 can be resistive heaters, Peltier devices, or other thermoelectric elements. Optionally, the nucleation elements 231, 233 can also be used to control the temperature of the skin 230. For example, the nucleation elements 231, 233 can include RF electrodes that cooperate to deliver RF energy to heat the skin 230 or deeper tissue.

Multiple applicators may be concurrently or sequentially used during a treatment session, and such applicators can include, without limitation, vacuum applicators, belt applicators, and so forth. Each applicator may be designed to treat identified portions of the patient's body, such as the chin, cheeks, forehead, back, shoulders, arms, pectoral areas, armpits, genital region, palms of hands, soles of feet and so forth. For example, a vacuum applicator may be applied at the back region, and the belt applicator may be applied around the thigh region, either with or without massage or vibration. Exemplary applicators and their configurations usable or adaptable for use with the treatment system 100 are described in, e.g., U.S. Pat. No. 8,834,547 and commonly assigned U.S. Pat. No. 7,854,754 and U.S. Patent Publication Nos. 2008/0077201, 2008/0077211, and 2008/0287839, which are incorporated by reference in their entireties.

Figure 6A:
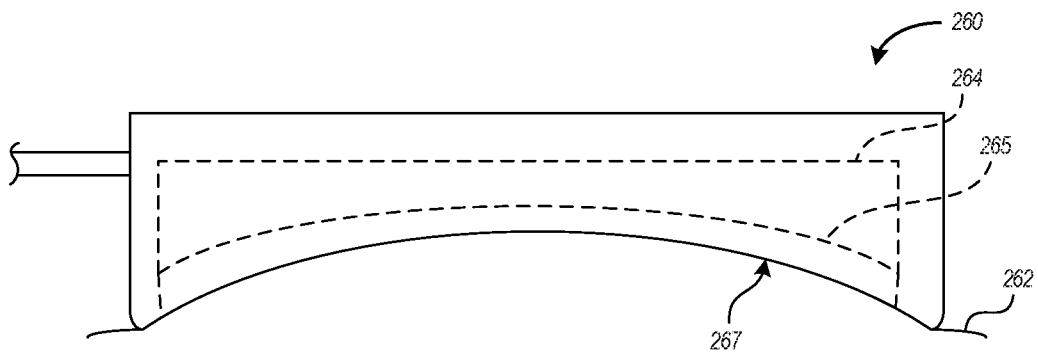
FIGS. 6A to 6C are schematic cross-sectional views of treatment devices in accordance with embodiments of the technology.
Figure 6B:
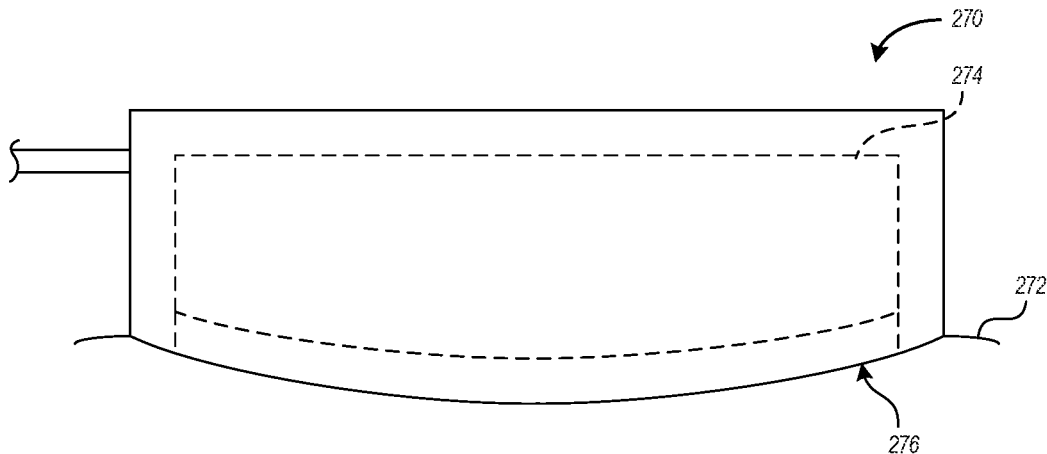
Figure 6C:
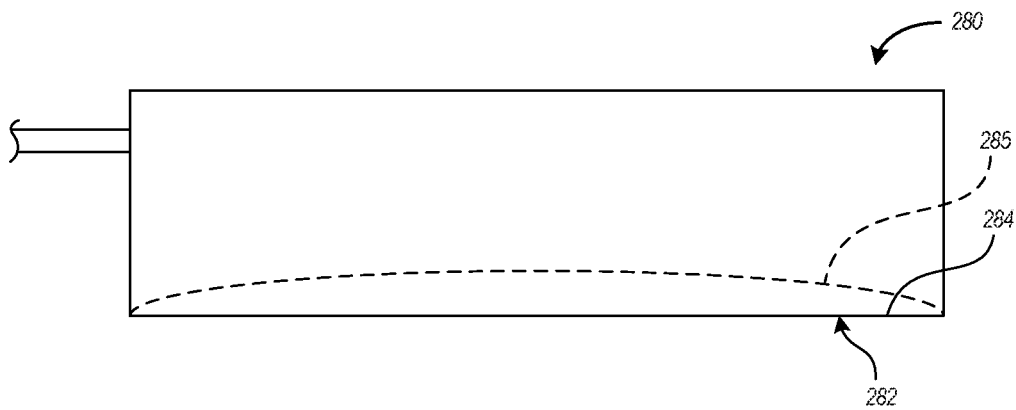

FIGS. 6A to 6C illustrate treatment devices suitable for use with treatment systems disclosed herein in accordance with embodiments of the technology. FIG. 6A is a schematic, cross-sectional view illustrating an applicator 260 for non-invasively removing heat from target areas of a subject 262. The applicator 260 can include a heat-exchanging unit or cooling device 264 (shown in phantom line) and an interface layer 265 (shown in phantom line). The interface layer 265 can have a rigid or compliant concave surface 267. When the applicator 260 is held against the subject, the subject's tissue can be pressed against the curved surface 267. In some treatments, the compliant concave surface 267 can be suitable for being applied to a subject's chin, cheek, forehead, or other contoured body area. One or more vacuum ports can be positioned along the surface 267 to draw the skin 262 against the surface 267. The configuration of the applicator 260 can be selected based on the treatment site.

FIG. 6B is a schematic, cross-sectional view illustrating an applicator 270 that can include a heat-exchanging unit 274 having a rigid or compliant convex surface 276 configured to be applied to concave regions of the subject. Advantageously, the convex surface 276 can spread tissue to reduce the distance between the convex surface 276 and targeted tissue under the convex surface 276. In some treatments, the applicator 270 can be applied to the axilla (i.e., armpit) region to affect apocrine sweat glands.

FIG. 6C is a schematic, cross-sectional view illustrating an applicator 280 including a surface 282 movable between a planar configuration 284 and a non-planar configuration 285 (shown in phantom). The surface 282 is capable of conforming to the treatment site to provide a large contact area. In some embodiments, the surface 282 can be sufficiently compliant to conform to highly contoured regions of a subject's face when the applicator 280 is pressed against facial tissue. In other embodiments, the applicator 280 can include actuators or other devices configured to move the surface 282 to a concave configuration, a convex configuration, or the like. The surface 282 can be reconfigured to treat different treatment sites of the same subject or multiple subjects.

Figure 6D:
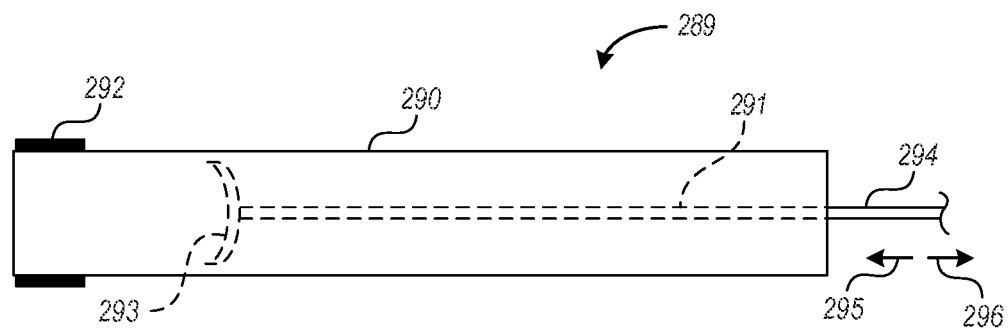
FIG. 6D is a side view of an applicator for treating discrete features in accordance with embodiments of the technology.

FIG. 6D is a side view of an applicator 289 configured to treat a targeted feature. Targeted features can be, without limitation, cysts, glands, or other discrete features. The applicator 289 can include a main housing 290, a cooling assembly 291, and a control element 292. The main housing 290 can be a tubular member that surrounds and protects the cooling assembly 291. The cooling assembly 291 can include, without limitation, a cooling device or element 293 ("cooling element 293") and a connector 294. The cooling element 293 can be connected to another device (e.g., a control tower or base unit) by the connector 294. The connector 294 can be a rod that is moved distally (indicated by arrow 295) or proximally (indicated by arrow 296) to move the cooling element 293 along a passageway of the housing 290. The connector 294 can include one or more conduits, wires, passageways, or other features for providing energy (e.g., electrical energy, radiofrequency energy, etc.), coolant, a vacuum, or the like. In some embodiments, the connector 294 can be an umbilical rod that provides energy, fluid, and/or suction. The applicator 289 can include sensors or other applicator components disclosed herein. For example, the applicator 289 can include sensors configured to measure tissue impedance, pressure applied to the subject, optical characteristics of tissue, and/or tissue temperatures in order to monitor tissue and, in some embodiments, to detect events, such as partial or complete freeze events.

Figure 6E:
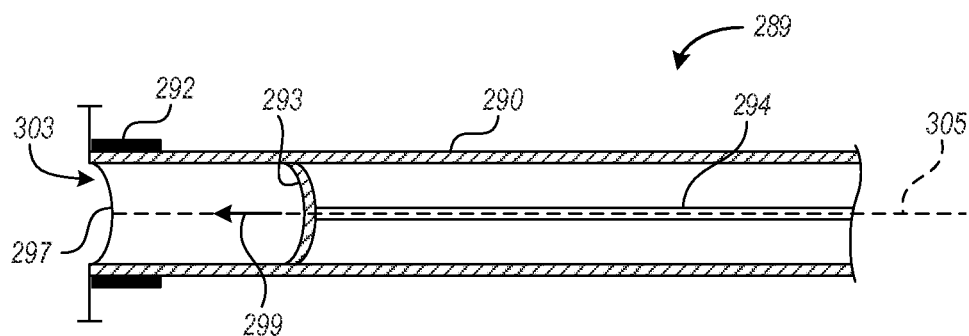
FIGS. 6E and 6F are cross-sectional views of a distal end of the applicator of FIG. 6D.

FIG. 6E is a cross-sectional view of a distal portion of the applicator 289. The cooling element 293 is spaced apart from an opening 303 for receiving a feature 297 to be treated. The connector 294 can be pushed distally (indicated by arrow 299) to move the cooling element 293 relative to a longitudinal axis 305 of the applicator 289. In some embodiments, the connector 294 is manually moved through the housing 290. In other embodiments, the applicator 289 can include or be used with a drive device configured to move the connector 294. The drive device can include, without limitation, one or more motors (e.g., drive motors, stepper motors, etc.), sensors (e.g., position sensors), controllers, or other components.

Figure 6F:
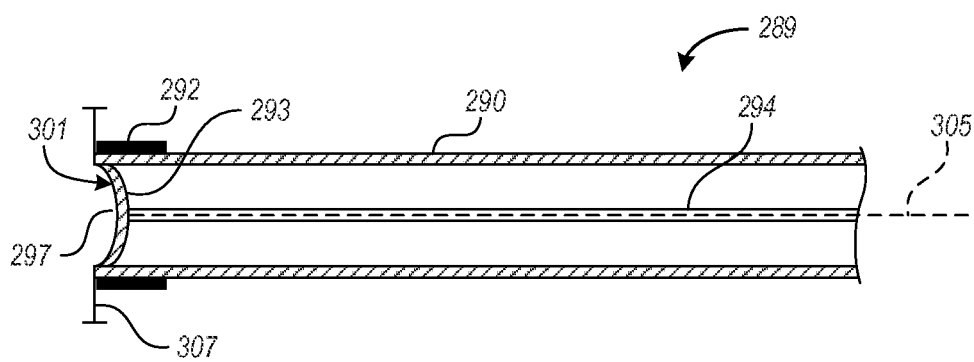

FIG. 6F is a cross-sectional view of the applicator 289 after the cooling element 293 thermally contacts the target feature 297. In some embodiments, the cooling element 293 can have a generally concave surface 301 for contacting a large area of the protruding target feature 297, such as a sebaceous cyst, sudoriferous cyst, cyst of Zeis, hidrocystoma, bulging gland, acne, or other treatable feature.

The control element 292 can be used to adjust the cooling element 293 by, for example, bending or otherwise adjusting the configuration of the cooling element 293. The curvature of the surface 301 can be increased or decreased by moving the control element 292 inwardly or outwardly, respectively. The control element 292 can include, without limitation, one or more clamps, bands, locking features, etc. for adjusting the configuration of the distal end of the main housing 290 and cooling element 293. The cooling element 293 can be flexible to comfortably engage the target features, such as a bulging cyst. In rigid embodiments, a physician can select a curved cooling element 293 with a configuration (e.g., a partially spherical shape, partially elliptical shape, etc.) selected based on, for example, the shape and/or configuration of targeted feature(s). The cooling element 293 can include, without limitation, one or more cooling devices, thermoelectric coolers, cooling channels, electrodes, heating elements, or other features for treating the target feature 297. After the cooling element 293 contacts the skin 307, the cooling element 293 can actively cool the target feature 297.

The applicator 289 can be used to cool/heat relatively small features that may be near sensitive non-targeted tissue. The size of the cooling element 293 can be selected to minimize treatment of non-targeted tissue. To treat features around the eyes, the applicator 289 can be selected such that most of the tissue received by the cooling element 293 is targeted tissue to avoid affecting surrounding tissue. In some procedures, the applicator 289 can be applied to the subject such that the targeted feature is positioned within the opening 303 (FIG. 6E). The cooling element 293 can be moved through the housing 290 and into thermal contact with the subject's skin 307. In some procedures, the cooling element 293 can be moved back and forth to adjust the applied pressure, provide a massaging effect, promote nucleation, or the like. The applicator 289 can treat a wide range of features or areas at various locations along the subject's body.

Figure 7:
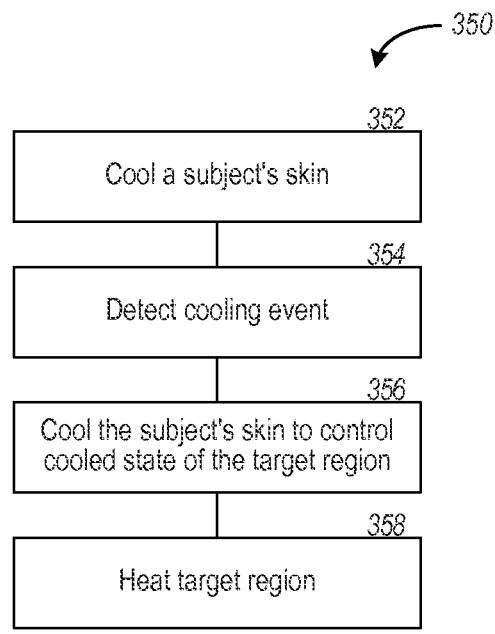
FIGS. 7 to 10 are flow diagrams illustrating methods for affecting target regions in accordance with embodiments of the technology.
Figure 8:
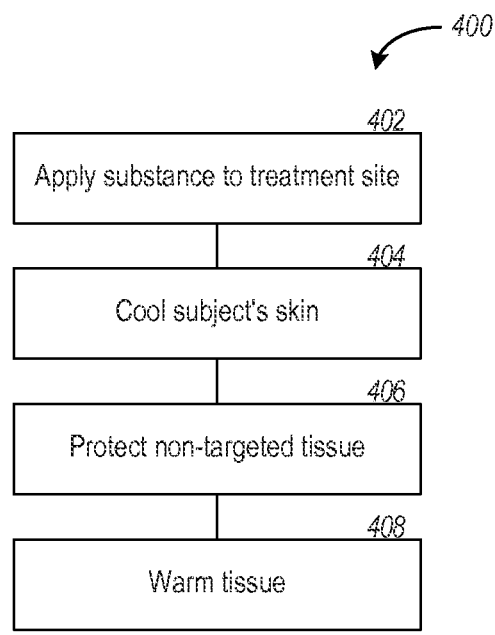

FIGS. 7 and 8 are flow diagrams illustrating methods for treating sites in accordance with embodiments of the technology. Although specific example methods are described herein, one skilled in the art is capable of identifying other methods that could be performed using embodiments disclosed herein. The methods are generally described with reference to the treatment system 100 of FIG. 3, but the methods may also be performed by other treatment systems with additional or different hardware and/or software components.

FIG. 7 is a flow diagram illustrating a method 350 for treating exocrine glands in accordance with embodiments of the technology. Generally, a subject's skin can be cooled to thermally affect a target region containing exocrine glands. Treatment can be monitored in order to keep tissue cooled for a sufficient length of time to affect the exocrine glands. Details of method 350 are discussed below.

At block 352, a treatment device is applied to a subject by placing its heat-exchanging surface or other feature in thermal contact with the subject's skin. The surface of the subject's skin can be continuously or periodically cooled to produce at least one cooling event (e.g., a partial freeze event, a complete freeze event, supercooling event, etc.) in a portion of the skin with exocrine glands. In treatments for acne, the targeted glands can be sebaceous glands and/or supporting structures, which may be in the epidermis and/or dermis. In treatments for excessive sweating, the targeted glands can be sweat glands and/or supporting structures.

Rapid cooling can create a thermal gradient with the coldest temperatures in the region of skin near the treatment device whereas rapid heating can create a thermal gradient with the highest temperatures in the region of skin near the treatment device. During cooling, skin can be frozen for a short enough duration to not establish a temperature equilibrium across the skin and adjacent subcutaneous tissue. Cryoprotectant(s) and/or warming cycle(s) can be used to inhibit freezing of the uppermost non-targeted layer or layers of skin (e.g., layers of the epidermis). In some procedures, a cryoprotectant can be applied to the treatment site to inhibit damage to the epidermis while cooling and freezing the dermal layer without causing freeze damage to subcutaneous tissue. As such, the combination of cryoprotectant and controlled cooling can produce a desired cooling zone, and cooling of the cooling zone can be controlled to either have a non-freeze cooling event, a partial freeze event or a total brief freeze event. In some embodiments, the treatment device can non-invasively produce a freeze event that begins within a predetermined period of time after the applicator begins cooling the patient's skin. The predetermined period of time can be equal to or shorter than about 10 seconds, 30 seconds, 60 seconds, 90 seconds, 120 seconds, or 150 seconds or longer periods and, in some embodiments, can be from between about 10 seconds to about 150 seconds, between about 30 seconds to about 150 seconds, or between about 60 seconds to about 150 seconds. In some embodiments, the predetermined period of time can be shorter than about 1, 2, 3, 4, 5, 6, 7, 8, 9, or 10 minutes. A controller (e.g., controller 114 of FIG. 2) can select the predetermined period of time for producing a cooling event based on the treatment temperatures, treatment sites, and/or cryotherapy to be performed. Alternatively, an operator can select the period of time for cooling and can enter it into the controller 114.

In some embodiments, the subject's skin can be cooled to produce a partial freeze event that includes at least some crystallization (e.g., formation of microscopic ice crystals) in intercellular material (e.g., fluid, cell components, etc.) and/or extracellular fluid. By avoiding extensive ice crystal formation that would cause frostbite or necrosis, partial freeze events can occur without excessive tissue damage. In some embodiments, the surface of the patient's skin can be cooled to a temperature no lower than about −40° C., −30° C., −20° C., −10° C., −5° C., or −3° C. to produce a partial freeze event in the skin without causing irreversible skin damage. In one example, the surface of the skin can be cooled to from about −40° C. to about 0° C., from about −30° C. to about 0° C., from about −20° C. to about 0° C., or from about −15° C. to about 0° C. or below about −10° C., −20° C., −20° C., −30° C., or −40° C. It will be appreciated that the surface of the skin can be cooled to other temperatures that are selected based on the mechanism of action.

At block 354, one or more events (e.g., freeze events) can be detected using one or more electrical components of the treatment device. During cooling, targeted tissue can reach a temperature below the freezing point of its biological tissue and fluids (e.g., approximately −1.8° C.). As tissue, fluids, and lipids freeze, crystals can form and energy associated with the latent heat of crystallization is released. The treatment system can determine the extent of freezing based on the detected temperature changes caused of crystallization. A relatively small positive change in tissue temperature can indicate a partial or total freeze event whereas a relatively large positive change in tissue temperature can indicate a complete freeze event. The sensor 167 (FIG. 2) and the sensor 227 of FIG. 5 can be freeze detect sensors capable of detecting the positive change in tissue temperature, and the treatment system can identify it as a freeze event. The treatment system can be programmed so that small temperature variations do not cause false alarms with respect to false events. Additionally or alternatively, the treatment systems may detect changes in the temperature of its components or changes in power supplied to treatment devices, or other components, to identify freeze events.

The treatment system 100 of FIG. 3 can use optical techniques to detect cooling events at block 354 of FIG. 7. For example, sensor 167 of FIG. 2 and sensors 217, 227 of FIG. 5 can be optical sensors capable of detecting changes in the optical characteristics of tissue caused by freezing. Optical sensors can include, without limitation, one or more energy emitters (e.g., light sources, light emitting diodes, etc.), detector elements (e.g., light detectors), or other components for non-invasively monitoring optical characteristics of tissue. In place of or in conjunction with monitoring using optical techniques, tissue can be monitored using electrical and/or mechanical techniques. In embodiments for measuring electrical impedance of tissue, the sensors (e.g., sensor 167 of FIG. 2 and sensors 217, 227 of FIG. 5) can include two electrodes that can be placed in electrical communication with the skin for monitoring electrical energy traveling between the electrodes via the tissue. In embodiments for measuring mechanical properties of tissue, the sensors disclosed herein can comprise one or more mechanical sensors which can include, without limitation, force sensors, pressure sensors, and so on.

At block 356, the treatment device and other treatment parameters can be controlled to control the temperature in the target region and, in some embodiments, includes periodically or continuously cooling the patient's tissue to keep a target region of skin in a cooled state (e.g., a frozen state) for a period of time. The treatment parameters can include, for example, cryoprotectant protocols, temperature profiles, treatment durations, number of cooling zones, characteristics of cooling zones, energy delivered to tissue, control parameters (e.g., control parameters for features such as vibration, massage, vacuum, and other treatment modes), or the like. For example, the skin within the cooling zone (e.g., event zone 232 of FIG. 5) can be kept frozen for a length of time selected based on the desired severity of the freeze injury. In short treatments, the period of time can be equal to or shorter than about 5, 10, 15, 20, or 25 seconds. In longer treatments, the period of time can be equal to or longer than about 25 seconds, 30 seconds, 45 seconds or 1, 2, 3, 4, 5, or 10 minutes. In some procedures, the treatment device can be controlled so that the skin is partially or completely frozen for no longer than, for example, 5 minutes, 10 minutes, 20 minutes, 30 minutes, 45 minutes, or 1 hour. In some examples, the skin is frozen for about 1 minute to about 5 minutes, about 5 minutes to about 10 minutes, about 10 minutes to about 20 minutes, about 20 minutes to about 30 minutes, or about 30 minutes to about 1 hour.

In some embodiments, the treatment system can control the treatment device so that the freeze event causes apoptotic damage to targeted glands but does not cause such damage to non-targeted tissue. In one example, the treatment device produces a partial freeze event short enough to prevent establishing equilibrium temperature gradients in the patient's skin. This allows freezing of shallow targeted tissue without substantially affecting deeper non-targeted tissue. Moreover, cells in the dermal layer can be affected to a greater extent than the cells in the subdermal layer (e.g., subcutaneous adipose tissue). In some procedures, the subdermal layer can be kept at a sufficiently high temperature (e.g., at or above 0° C.) while the shallower dermal tissue experiences the partial or total freeze event. The treatment system can also control operation of the treatment devices to thermally injure tissue to cause fibrosis, which increases the amount of connective tissue in a desired tissue layer (e.g., epidermis and/or dermis) to increase the firmness and appearance of the skin. In other treatments, the treatment system controls one or more applicators to supercool and freeze dermal tissue.

At block 358, the frozen region can be thawed by heating it and/or applying a topical substance in order to minimize, reduce, or limit tissue damage. The applicator can thaw the patient's skin after the freeze event occurs and after a period of time has transpired. The period of time can be equal to or shorter than about 5, 10, 15, 20, or 25 seconds or about 1, 2, 3, 4, 5, 6, 7, 8, 9, or 10 minutes. In one example, the uppermost skin layer(s) can be periodically heated to a temperature above the skin's freezing point to provide freeze protection thereto. The applicator can include one or more thermal elements (e.g., resistive heaters, electromagnetic energy emitters, Peltier devices, etc.) for heating tissue. For example, a cooling element 109 of FIG. 2 can be a Peltier device or one or more resistive heaters capable of generating heat for thawing tissue. In some embodiments, the applicator 104 of FIGS. 2 and 3 can have separate and independently controlled cooling elements and heating elements that can cooperate to provide precise temperature control for freezing and thawing/warming cycles. In some embodiments, applicators may stop cooling tissue to allow frozen tissue to passively warm and thaw.

The treatment systems disclosed herein can monitor the location and/or movement of the treatment devices and may prevent false or inaccurate determinations of treatment events based on such monitoring. During treatment, the treatment device may move which may cause it to contact a warmer area of skin, to no longer contact the skin, and so on. This may cause the treatment system to register a difference in temperature that is inconsistent with a normal treatment. Controllers (e.g., controller 114 of FIG. 3) may be programmed to differentiate between these types of temperature increases and a temperature increase associated with freezing. U.S. Pat. No. 8,285,390 discloses techniques for monitoring and detecting freeze events and applicator movement and is incorporated by reference in its entirety. Additionally, treatment systems can provide an indication or alarm to alert the operator to the source of this temperature increase. In the case of a temperature increase not associated with an event, the system may also suppress false indications, while in the case of a temperature increase associated with freezing, the system take any number of actions based on that detection.

FIG. 8 is a flow diagram illustrating a method 400 in accordance with an aspect of the present technology. Generally, a substance can be applied to the treatment site. The applicator can be applied to the treatment site and can cool tissue while the cryoprotectant protects non-targeted tissue. A cooled region (e.g., a frozen or non-frozen region) can be warmed (e.g., thawed) to inhibit or limit thermal damage to tissue. In some embodiments, the treatment site can be monitored to keep tissue frozen or non-frozen but yet cold for a sufficient length of time to affect glands. Details of method 400 are discussed below.

At block 402, a substance can be applied to the subject's skin to improve heat transfer between the treatment device and the subjects skin, selectively protect non-target tissues from thermal damage (e.g., freeze damage due to crystallization), and/or initiate/control thermal events. In one embodiment, the substance can be a cryoprotectant that prevents, inhibit, or limits damage to non-targeted tissue. Additionally or alternatively, the cryoprotectant can allow, for example, the treatment device to be pre-cooled prior to being applied to the subject for more efficient treatment. Further, the cryoprotectant can also enable the treatment device to be maintained at a desired low temperature while preventing ice formation on the cooled surface of the treatment device, and thus reduces the delay in reapplying the treatment device to the subject. Yet another aspect of the technology is the cryoprotectant may prevent the treatment device from freezing to the subject's skin. Certain cryoprotectants can allow microscopic crystals to form in the tissue but can limit crystal growth that would cause cell destruction and, in some embodiments, can allow for enhanced uptake or absorption and/or retention in target glands and/or surrounding tissue prior to and during cooling.

Some embodiments according to the present technology may use a cryoprotectant with a freezing point depressant that can assist in preventing freeze damage that would destroy cells. Suitable cryoprotectants and processes for implementing cryoprotectants are described in commonly-assigned U.S. Patent Publication No. 2007/0255362. The cryoprotectant may additionally include a thickening agent, a pH buffer, a humectant, a surfactant, and/or other additives and adjuvants as described herein. Freezing point depressants may include, for example, propylene glycol (PG), polyethylene glycol (PEG), dimethyl sulfoxide (DMSO), or other suitable alcohol compounds. Cryoprotectant can be delivered to the surface of the patient's skin for a period of time which is short enough to not significantly inhibit the initiation of the partial freeze event in dermal tissue but which is long enough to provide substantial protection to non-targeted tissue epidermal. Multiple cryoprotectants can be used to protect different tissue layers. For example, a first cryoprotectant for protecting deep tissue can be applied before a second cryoprotectant for protecting shallow tissue because the first cryoprotectant may require a longer delivery time to reach the deeper tissue.

The rate of cryoprotectant delivery can be selected based on the characteristics of the cryoprotectant and the desired amount of tissue protection. In one specific treatment, an interface member is placed directly over the target area, and the treatment device with a disposable sleeve or liner is placed in contact with the interface member. The interface member can be a cotton pad, a gauze pad, a pouch, or a container with a reservoir containing a volume of cryoprotectant or other flowable conductive substance. The interface member can include, for example, a non-woven cotton fabric pad saturated with cryoprotectant that is delivered at a desired delivery rate. Suitable pads include Webril™ pads manufactured by Covidien of Mansfield, Mass. Further details regarding interface members and associated systems and methods of use are described in commonly-assigned U.S. Patent Publication No. 2010/0280582.

In block 404, the subjects skin can be cooled using a treatment device in thermal contact with the subject's skin. The surface of the subject's skin can be continuously or periodically cooled to produce a freeze event (e.g., partial freeze event, complete freeze event, etc.). The description of block 352 in FIG. 7 applies equally to block 404 in FIG. 8.

In block 406, thermal energy can be delivered to the surface of the skin before, during, and/or after skin cooling to protect non-targeted tissue in the uppermost region of the skin. In some embodiments, the dermal tissue with glands below the epidermis can be frozen/supercooled. The treatment device can heat the surface of the skin to warm the epidermis or portions thereof to prevent, inhibit, or limit damage to non-targeted epidermal tissue while the region of dermal tissue with glands remains in a frozen/supercooled state. If the targeted region is supercooled, it can be controllably frozen using one or more nucleation initiators (e.g., mechanical perturbation such as vibration, ultrasound pulse, change in pressure, etc.).

Heat can be delivered transcutaneously to the subcutaneous layer to protect the subcutaneous tissue. For example, subcutaneous tissue can be heated prior to tissue cooling the subject's skin at block 404. In some procedures, the subcutaneous tissue can be periodically heated (e.g., heated using radiofrequency energy) during skin cooling. Some embodiments, the skin can be alternatingly heated and cooled. The heating cycles can be used to keep the subcutaneous tissue at or above a threshold temperature (e.g., above its freezing point) to avoid freeze damage to the subcutaneous layer. The cooling cycles can be used to periodically cool the targeted dermal tissue and/or epidermal tissue. In some embodiments, the topical substance can be applied in order to minimize, reduce, or limit tissue damage.

At block 408, the frozen region can be warmed (e.g., thawed). In freeze event embodiments, the applicator can thaw the patient's skin after the freeze event occurs and after a period of time has transpired. The thawing process at block 408 can be the same as the thawing process of block 358 of FIG. 7.

E. Treatments Using Supercooling

Figure 9:
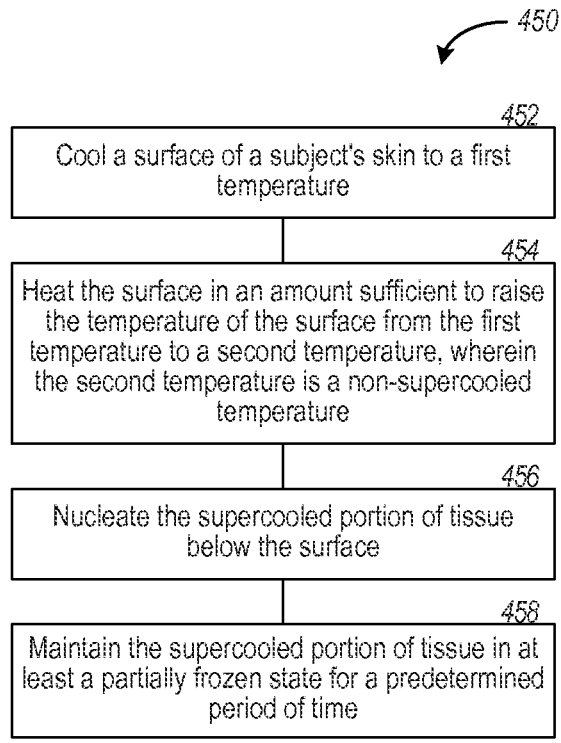
Figure 10:
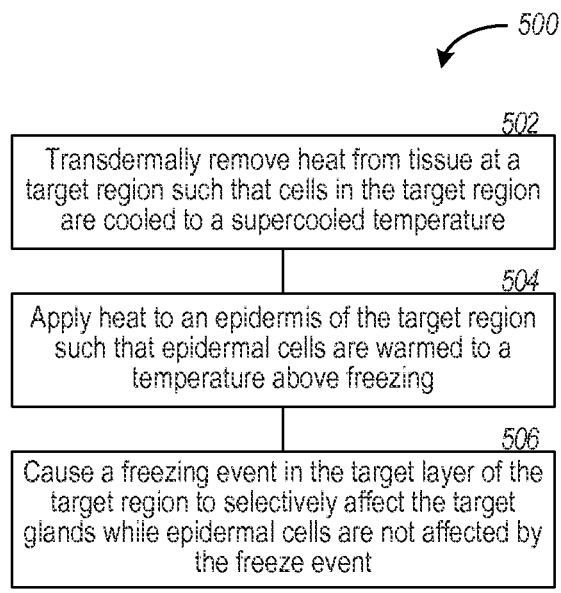

FIGS. 9 and 10 are flow diagrams illustrating methods for supercooling regions in accordance with embodiments of the technology. Generally, a surface of a human subject's skin can be cooled to a temperature no lower than −40° C. to avoid unwanted skin damage and so that the temperature of at least a portion of tissue is in a supercooled state. The surface of the skin can be heated to bring shallow non-targeted tissue out of the supercooled state while the deeper targeted region remains in the supercooled state. The supercooled targeted region can be nucleated due to a perturbation that causes at least partial or total freezing that destroys or damages targeted cells, for example, due to crystallization of intracellular and/or extracellular fluids. In one embodiment, mechanical perturbation and/or other catalyst for nucleation (e.g., RF energy, alternating electric fields, etc.) within the target tissue can be provided only following a protective increase of a temperature of non-targeted epidermal layers. The mechanical perturbations can be vibrations, ultrasound pulses, and/or changes in pressure. The non-targeted layers can be warmed enough to avoid freezing of non-targeted tissue upon nucleation. The treatment system 100 (FIG. 3) can utilize applicators disclosed herein to perform such supercooling methods.

FIG. 9 is a flow diagram illustrating a method 450 in accordance with an aspect of the present technology. An early stage of the method 450 can include cooling a surface of a human subject's skin to a first temperature (block 452). The first temperature can be, for example, between about −10° C. and −40° C. such that a portion of tissue below the surface is in a supercooled state. In other embodiments, the first temperature can be a temperature between about −15° C. and −25° C., a temperature between about −20° C. and about −30° C., or other temperature below a freezing temperature.

In block 454, the surface of the human subject's skin is heated an amount sufficient to raise the skin surface temperature from the first temperature to a second temperature, which can be a non-supercooled temperature, while the targeted region remains in the supercooled state. For example, the treatment system can be used to heat the surface of the skin to a temperature higher than about 0° C., higher than about 5° C., higher than about 10° C., higher than about 20° C., higher than about 30° C., or higher than about 35° C. There can be a temperature gradient between the targeted tissue and the skin surface such that most of the non-targeted tissue (e.g., epidermis) is at a non-supercooled temperature.

In block 456, the supercooled portion of tissue below the skin surface can be nucleated to cause at least some fluid and cells in the supercooled tissue to at least partially or totally freeze. In one embodiment, nucleation of the supercooled tissue is caused by a mechanical perturbation, ultrasound, massaging, or other suitable nucleation initiator. Warmed cells residing at the surface of the human subject's skin do not freeze at block 456. As such, cells at the skin surface are protected without using a chemical cryoprotectant. The chemical cryoprotectants can be selected to inhibit or limit hyperpigmentation or hypopigmentation.

In block 458, the supercooled tissue can be maintained in the at least partially or totally frozen state for a predetermined period of time longer than, for example, about 10 seconds, 12 seconds, 15 seconds, or 20 seconds. In various arrangements, the supercooled tissue in a cooling zone (e.g., event zone 232 of FIG. 5) can be maintained in the at least partially or totally frozen state for a duration of time sufficient to treat acne, improve a quality of hair, treat hyperhidrosis, etc. In certain embodiments, the skin is cooled/heated to maintain targeted tissue in at least a partially or totally frozen state for the predetermined time longer than about 10 seconds, longer than about 12 seconds, longer than about 15 seconds, or longer than about 20 seconds.

FIG. 10 illustrates a method 500 for affecting a target region in a human subject's body in accordance with another embodiment of the present technology. The method 500 can include transdermally removing heat from tissue at a target region such that the target region is cooled to a supercooled temperature (block 502). The supercooled temperature can be, for example, below about 0° C. or within a range from about 0° C. to about −20° C., from about −10° C. to about −30° C., from about −20° C. to about −40° C., or no lower than about −40° C. Cryoprotectants can be used when cooling tissue to very low temperatures, including temperatures lower than −40° C.

In block 504, the method 500 includes applying heat to an epidermis of the target region to warm epidermal cells in the target region to a temperature above freezing while glands in the dermis are at or near the supercooled temperature. For example, the step of applying heat can include warming a portion of most of the epidermal layer under the treatment device to a temperature above about 0° C., about 5° C., about 10° C., about 20° C., about 25° C., or about 32° C. Warming can be accomplished by thermal heaters (e.g., heaters 235 in FIG. 5) disposed on a surface of the applicator contacting or confronting a skin surface. Alternatively, if deeper tissue is not targeted, such tissue could be warmed using focused electrical currents which focus their energy below the skin surface, focused ultrasound which has a focal point for its energy below the skin surface, or RF energy. In such embodiments, the elements 235 of FIG. 5 can be electrodes or transducers.

In block 506, a freeze event in the dermal layer can selectively affect the targeted glands while epidermal cells are not affected by the freeze event. The method 500 can include providing at least one of vibration, mechanical pressure, and ultrasound pulses to the target region to cause such a freeze event. In various arrangements, the freeze event can cause at least partial crystallization of a plurality of gland cells in the target region. Beneficially, the epidermal cells are protected to avoid or limit freeze damage to those cells.

In some methods 500, supercooled temperatures of the targeted tissue can be achieved without initiating nucleation by cooling the treatment site at a relatively slow rate (e.g., the temperature profile can cause a slow cooling of the tissue at the target region) at block 502. For example, the rate of cooling can be either equal to, slower or faster than about 0.5, 1, 2, 3, 4, 5, 6, 7, 8, 9 or 10 degrees C. per minute. A preferred rate of cooling is about either 2, 4, or 6 degrees C. per minute. Additionally or alternatively, a treatment device can apply a generally constant pressure during cooling to the supercooled temperature range to avoid pressure changes that would cause inadvertent nucleation. In a further embodiment, the targeted tissue can be cooled while the patient is held still (e.g., without movement of the treatment site) to avoid mechanically disturbing the supercooled tissue and unintentionally causing crystallization. At block 504, the temperature of the non-targeted surface tissue can be warmed to a non-freezing temperature and/or a non-supercooled temperature prior to perturbation and subsequent freezing. In one embodiment, the warming cycle of the temperature profile can occur quickly such that the underlying and/or targeted tissue remains in the supercooled state throughout the warming cycle. The supercooled tissue can then be nucleated at block 506.

Various aspects of the methods disclosed herein can include cosmetic treatment methods for treating the target region of a human subject's body to achieve a cosmetically beneficial alteration of a portion of tissue within the target region. Such cosmetic methods can be administered by a non-medically trained person. The methods disclosed herein can also be used to (a) improve the appearance of skin by tightening the skin, improving skin tone and texture, eliminating or reducing wrinkles, increasing skin smoothness, thickening the skin, (b) improve the appearance of cellulite, and/or (c) treat sebaceous glands, hair follicles, and/or sweat glands.

F. Suitable Computing Environments

Figure 11:
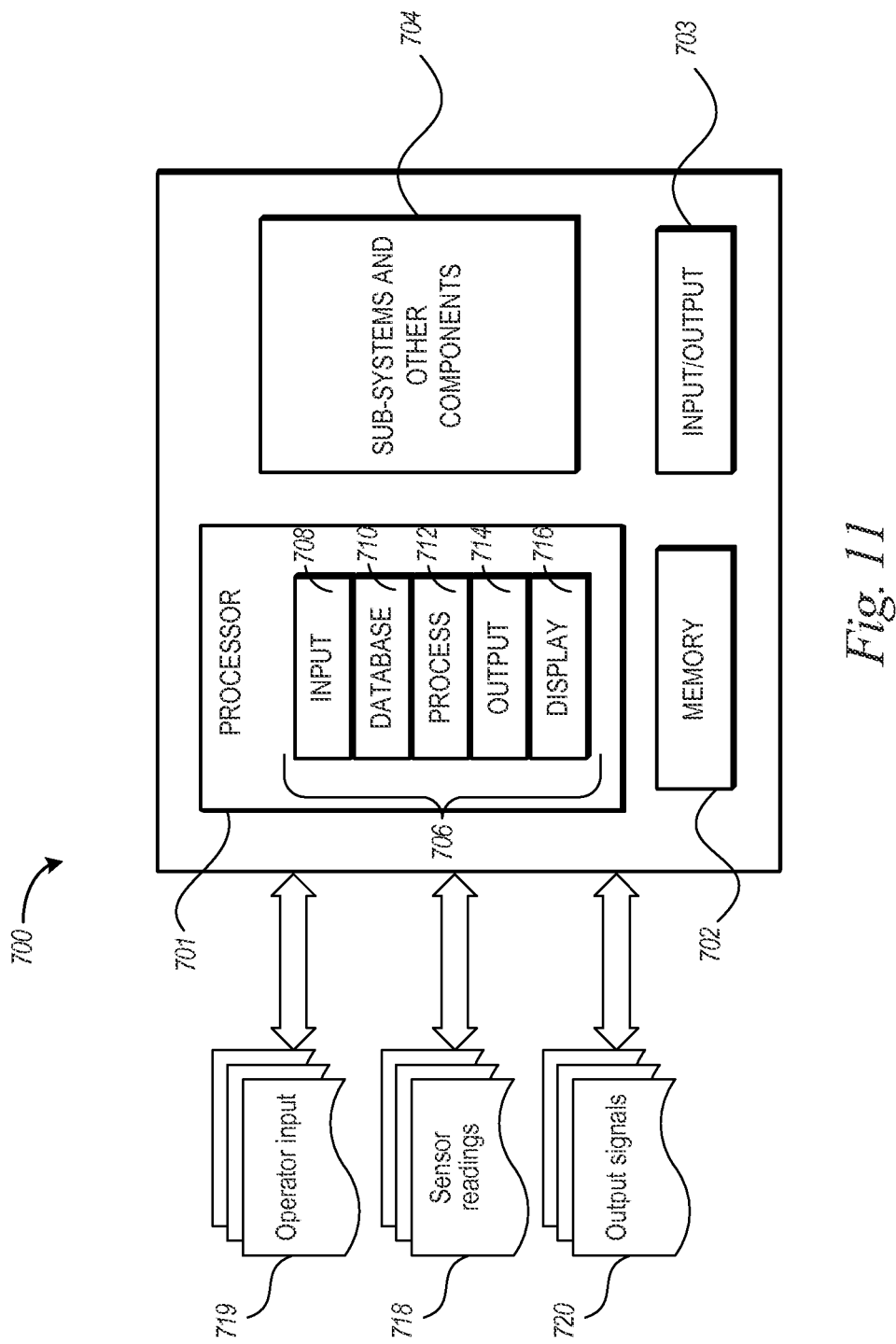
FIG. 11 is a schematic block diagram illustrating computing system software modules and subcomponents of a computing device suitable to be used in treatment systems in accordance with embodiments of the technology.

FIG. 11 is a schematic block diagram illustrating subcomponents of a computing device 700 suitable for the system 100 of FIG. 3 in accordance with an embodiment of the disclosure. The computing device 700 can include a processor 701, a memory 702 (e.g., SRAM, DRAM, flash, or other memory devices), input/output devices 703, and/or subsystems and other components 704. The computing device 700 can perform any of a wide variety of computing processing, storage, sensing, imaging, and/or other functions. Components of the computing device 700 may be housed in a single unit or distributed over multiple, interconnected units (e.g., though a communications network). The components of the computing device 700 can accordingly include local and/or remote memory storage devices and any of a wide variety of computer-readable media.

As illustrated in FIG. 11, the processor 701 can include a plurality of functional modules 706, such as software modules, for execution by the processor 701. The various implementations of source code (i.e., in a conventional programming language) can be stored on a computer-readable storage medium or can be embodied on a transmission medium in a carrier wave. The modules 706 of the processor can include an input module 708, a database module 710, a process module 712, an output module 714, and, optionally, a display module 716.

In operation, the input module 708 accepts an operator input 719 via the one or more input/output devices described above with respect to FIG. 5, and communicates the accepted information or selections to other components for further processing. The database module 710 organizes records, including patient records, treatment data sets, treatment profiles and operating records and other operator activities, and facilitates storing and retrieving of these records to and from a data storage device (e.g., internal memory 702, an external database, etc.). Any type of database organization can be utilized, including a flat file system, hierarchical database, relational database, distributed database, etc.

In the illustrated example, the process module 712 can generate control variables based on sensor readings 718 from sensors (e.g., sensor 167 of FIG. 2, the temperature measurement components 217 and 227 of FIG. 5, etc.) and/or other data sources, and the output module 714 can communicate operator input to external computing devices and control variables to the controller 114 (FIGS. 3 and 5). The display module 816 can be configured to convert and transmit processing parameters, sensor readings 818, output signals 720, input data, treatment profiles and prescribed operational parameters through one or more connected display devices, such as a display screen, printer, speaker system, etc. A suitable display module 716 may include a video driver that enables the controller 114 to display the sensor readings 718 or other status of treatment progression.

In various embodiments, the processor 701 can be a standard central processing unit or a secure processor. Secure processors can be special-purpose processors (e.g., reduced instruction set processor) that can withstand sophisticated attacks that attempt to extract data or programming logic. The secure processors may not have debugging pins that enable an external debugger to monitor the secure processor's execution or registers. In other embodiments, the system may employ a secure field programmable gate array, a smartcard, or other secure devices.

The memory 702 can be standard memory, secure memory, or a combination of both memory types. By employing a secure processor and/or secure memory, the system can ensure that data and instructions are both highly secure and sensitive operations such as decryption are shielded from observation. The memory 702 can contain executable instructions for cooling the surface of the subject's skin to a temperature and controlling treatment devices in response to, for example, detection of a partial or complete freeze events. The memory 702 can include thawing instructions that, when executed, causes the controller to control the applicator to heat tissue. In some embodiments, the memory 702 stores instructions that can be executed to control the applicators to perform the methods disclosed herein without causing undesired effects, such as significantly lightening or darkening skin one of more days after the freeze event ends. The instructions can be modified based on patient information and treatments to be performed. Other instructions can be stored and executed to perform the methods disclosed herein.

Suitable computing environments and other computing devices and user interfaces are described in commonly assigned U.S. Pat. No. 8,275,442, entitled "TREATMENT PLANNING SYSTEMS AND METHODS FOR BODY CONTOURING APPLICATIONS," which is incorporated herein in its entirety by reference.

G. Conclusion

It will be appreciated that some well-known structures or functions may not be shown or described in detail, so as to avoid unnecessarily obscuring the relevant description of the various embodiments. Although some embodiments may be within the scope of the technology, they may not be described in detail with respect to the Figures. Furthermore, features, structures, or characteristics of various embodiments may be combined in any suitable manner. The technology disclosed herein can be used for improving skin and skin conditions and to perform the procedures disclosure in U.S. Provisional Application Ser. No. 61/943,250, filed Feb. 21, 2014, U.S. Pat. No. 7,367,341 entitled "METHODS AND DEVICES FOR SELECTIVE DISRUPTION OF FATTY TISSUE BY CONTROLLED COOLING" to Anderson et al., and U.S. Patent Publication No. US 2005/0251120 entitled "METHODS AND DEVICES FOR DETECTION AND CONTROL OF SELECTIVE DISRUPTION OF FATTY TISSUE BY CONTROLLED COOLING" to Anderson et al., the disclosures of which are incorporated herein by reference in their entireties. The technology disclosed herein can target tissue for tightening the skin, improving skin tone or texture, eliminating or reducing wrinkles, increasing skin smoothness as disclosed in U.S. Provisional Application Ser. No. 61/943,250.

Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number, respectively. Use of the word "or" in reference to a list of two or more items covers all of the following interpretations of the word: any of the items in the list, all of the items in the list, and any combination of the items in the list. In those instances where a convention analogous to "at least one of A, B, and C, etc." is used, in general such a construction is intended in the sense of the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense of the convention (e.g., " a system having at least one of A, B, or C" would include but not be limited to systems that have A alone, B alone, C alone, A and B together, A and C together, B and C together, and/or A, B, and C together, etc.).

Any patents, applications and other references, including any that may be listed in accompanying filing papers, are incorporated herein by reference. Aspects of the described technology can be modified, if necessary, to employ the systems, functions, and concepts of the various references described above to provide yet further embodiments. While the above description details certain embodiments and describes the best mode contemplated, no matter how detailed, various changes can be made. Implementation details may vary considerably, while still being encompassed by the technology disclosed herein. The various aspects and embodiments disclosed herein are for purposes of illustration and are not intended to be limiting, with the true scope and spirit being indicated by the following claims.

What is claimed is:

1. A treatment system for treating a subject's glands, the glands being either sebaceous glands or sweat glands, the treatment system comprising:
    an applicator configured to be applied to the subject and including a cooling device for cooling the subject's skin at a treatment site to a temperature low enough and for a first period of time long enough to produce a freeze event in the skin, the temperature being higher than −40 degrees C.; and
    a controller programmed with instructions for causing the cooling device to continue to cool the subject's skin after the treatment system detects the freeze event so that the freeze event lasts a second period of time to substantially alter secretion levels of the glands without causing hypopigmentation of a significant amount of the subject's epidermis, which is directly between the cooling device and the tissue that experiences the freeze event, within one or more days after the freeze event ends, the second period of time being longer than 10 seconds.

2. The treatment system of claim 1, wherein the controller is programmed to control the cooling device to continue cooling the subject's skin after detection of the freeze event to maintain at least a partially frozen state of a portion of the skin with the glands so as to decrease the secretion levels of the glands.

3. The treatment system of claim 1, wherein the cooling device has a freeze detect sensor and a thermoelectric cooler, wherein the controller is configured to receive output from the freeze detect sensor and to cause the thermoelectric cooler to continue to cool the surface of the subject's skin for the second period of time after the freeze detect sensor detects at least partial freezing of the skin.

4. The treatment system of claim 1, wherein the controller is programmed to control operation of the cooling device to cool the subject's skin using the cooling device such that ice crystals are present in the skin for a sufficient length of time to injure the glands without causing necrosis.

5. The treatment system of claim 1, wherein the controller is programmed to cool the subject's skin for the second period of time and to a temperature sufficient to injure the subject's dermis and glands therein without substantially injuring the subject's subcutaneous adipose tissue.

6. The treatment system of claim 5, wherein the second period of time is less than about 40 minutes.

7. The treatment system of claim 1, wherein the controller is programmed to cause the treatment system to supply thermal energy to the surface of the skin before, during, and/or after skin cooling to inhibit freeze damage to the subject's epidermis.

8. The treatment system of claim 1, wherein the controller is programmed to control operation of the treatment system so that the treatment system promotes nucleation in supercooled tissue to initiate the freeze event.

9. The treatment system of claim 1, wherein the controller is programmed with thawing instructions that, when executed after the second period of time, cause the applicator to heat the treatment site and thaw the subject's frozen tissue.

10. The treatment system of claim 1, wherein the controller is programmed to control the treatment system such that the freeze event causes apoptotic damage to tissue at the treatment site and does not cause necrotic damage to tissue at the treatment site.

11. The treatment system of claim 1, wherein the applicator includes a curved cooling device movable away from and towards a targeted feature of the subject while the applicator is applied to the subject.

12. The treatment system of claim 11, wherein the cooling device is configured to receive and cool a sebaceous cyst.

13. A treatment system for treating a subject's sebaceous glands or sweat glands, the treatment system comprising:
    an applicator configured to be applied to the subject and including a cooling device for cooling the subject's skin at a treatment site to a temperature low enough and for a first period of time long enough to produce a cooling event in the skin, the temperature being higher than −40 degrees C.; and
    a controller programmed with instructions for causing the cooling device to cool the surface of the skin for a second period of time and to a temperature sufficiently low to injure the subject's dermis and the glands therein but without injuring the subject's subcutaneous adipose tissue and without causing significant lightening of any portion of an upper region of the skin at the treatment site within one day after the cooling event terminates, the upper region of the skin is located directly between the injured glands and the surface of the skin contacted by the cooling device, the second period of time being less than about 40 minutes.

\* \* \* \* \*